(12) United States Patent
Redinbo

(10) Patent No.: US 9,334,288 B2
(45) Date of Patent: May 10, 2016

(54) SELECTIVE β-GLUCURONIDASE INHIBITORS AS A TREATMENT FOR SIDE EFFECTS OF CAMPTOTHECIN ANTINEOPLASTIC AGENTS

(71) Applicant: The University of North Carolina at Chapel Hill, Chapel Hill, NC (US)

(72) Inventor: Matthew R. Redinbo, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/033,920

(22) Filed: Sep. 23, 2013

(65) Prior Publication Data

US 2015/0051205 A1 Feb. 19, 2015

Related U.S. Application Data

(63) Continuation of application No. 13/514,418, filed as application No. PCT/US2010/059690 on Dec. 9, 2010, now Pat. No. 8,557,808.

(60) Provisional application No. 61/285,265, filed on Dec. 10, 2009, provisional application No. 61/408,032, filed on Oct. 29, 2010.

(51) Int. Cl.

| | |
|---|---|
| *A61K 31/335* | (2006.01) |
| *A61K 31/00* | (2006.01) |
| *A61K 31/38* | (2006.01) |
| *A61K 31/435* | (2006.01) |
| *A61K 45/06* | (2006.01) |
| *A61K 31/381* | (2006.01) |
| *A61K 31/4704* | (2006.01) |
| *A61K 31/4745* | (2006.01) |
| *A61K 31/496* | (2006.01) |
| *A61K 31/519* | (2006.01) |
| *A61K 31/5377* | (2006.01) |
| *C07D 495/14* | (2006.01) |
| *C07D 215/227* | (2006.01) |
| *C07D 317/50* | (2006.01) |
| *C07D 333/38* | (2006.01) |
| *C07D 487/04* | (2006.01) |
| *C07D 495/04* | (2006.01) |

(52) U.S. Cl.
CPC .............. *C07D 495/14* (2013.01); *A61K 31/00* (2013.01); *A61K 31/335* (2013.01); *A61K 31/38* (2013.01); *A61K 31/381* (2013.01); *A61K 31/435* (2013.01); *A61K 31/4704* (2013.01); *A61K 31/4745* (2013.01); *A61K 31/496* (2013.01); *A61K 31/519* (2013.01); *A61K 31/5377* (2013.01); *A61K 45/06* (2013.01); *C07D 215/227* (2013.01); *C07D 317/50* (2013.01); *C07D 333/38* (2013.01); *C07D 487/04* (2013.01); *C07D 495/04* (2013.01)

(58) Field of Classification Search
CPC ..... A61K 31/335; A61K 31/00; A61K 31/38; A61K 31/435; A61K 45/06; A61K 31/381; A61K 31/4704; A61K 31/4745; A61K 31/496; A61K 31/519; A61K 31/5377
See application file for complete search history.

(56) References Cited

U.S. PATENT DOCUMENTS 8,557,808 B2 * 10/2013 Redinbo et al. ............. 514/232.8
2007/0287706 A1 12/2007 Dickson et al.

FOREIGN PATENT DOCUMENTS

| EP | 0 558 753 A1 | 9/1993 |
|---|---|---|
| EP | 1 197 214 A1 | 4/2002 |

OTHER PUBLICATIONS

Chen, Y, et al., "Synthesis, cytotoxicity, and anti-inflammatory evaluation of 2-(furan-2-yl)-4-(phenoxy)quinolone derivatives. Part 4," *Bioorganic & Medicinal Chemistry*, 2006, vol. 14, pp. 4373-4378.
Fittkau, M., et al., "Saccharic acid 1.4-lactone protects against CPT-11-induced mucosa damage in rats," *J Cancer Res Clin Oncol*, 2004, vol. 130, pp. 388-394.
Jain, S., et al., "Structure of human β-glucuronidase reveals candidate lysomal targeting and active-site mofits," *nature structural biology*, 1996, vol. 3(4), pp. 375-381.
Klei, H., et al., GenBank Direct Submission, "Human Beta-Glucuronidase At 1.7 A Resolution," MMDB ID: 78428, PDB ID: 3HN3, 2009, 2 pages.
Russell, W., et al., "Identification and Cloning of *gusA*, Encoding a New β-Glucuronidase from *Lactobacillus gasseri* ADH," *Applied and Environmental Microbiology*, 2001, vol. 67(3), pp. 1253-1261.
Takasuna, K., et al, "Inhibition of intestinal microflora β-glucuronidase modifies the distribution of the antitumor agent, irinotecan hydrochloride (CPT-11) in rats," *Cancer Chemother Pharmacol*, 1998, vol. 42, pp. 280-286.
Wallace, B., et al., GenBank Direct Submission, "Crystal Structure of Selenomethionine Substituted *E. Coli* Beta-Glucuronidase," MMDB ID: 86213, PDB ID: 3K4A, 2009, 1 page.
Wallace, B., et al., "Alleviating Cancer Drug Toxicity by Inhibiting a Bacterial Enzyme," *Science*, 2010, vol. 330, pp. 831-835.

\* cited by examiner

*Primary Examiner* — Samantha Shterengarts
(74) *Attorney, Agent, or Firm* — Alston & Bird LLP

(57) ABSTRACT

Compounds, compositions and methods are provided that comprise selective β-glucuronidase inhibitors for both aerobic and anaerobic bacteria, especially enteric bacteria normally associated with the gastrointestinal tract. The compounds, compositions and methods can be for inhibiting bacterial β-glucuronidase and for improving efficacy of camptothecin-derived antineoplastic agents or glucuronidase-substrate agents or compounds by attenuating the side effects caused by reactivation by bacterial β-glucuronidases of glucuronidated metabolites of camptothecin-derived antineoplasatic agents or glucuronidase-substrate agents or compounds.

16 Claims, 22 Drawing Sheets

A.

B.

SEQUENCE LISTING

<160> NUMBER OF SEQ ID NOS: 2

<210> SEQ ID NO 1
<211> LENGTH: 603
<212> TYPE: PRT
<213> ORGANISM: Escherichia coli

<400> SEQUENCE: 1

```
His Leu Arg Pro Val Glu Thr Pro Thr Arg Glu Ile Lys Lys Leu Asp
  1               5                  10                  15

Gly Leu Trp Ala Phe Ser Leu Asp Arg Glu Asn Cys Gly Ile Asp Gln
             20                  25                  30

Arg Trp Trp Glu Ser Ala Leu Gln Glu Ser Arg Ala Ile Ala Val Pro
         35                  40                  45

Gly Ser Phe Asn Asp Gln Phe Ala Asp Ala Asp Ile Arg Asn Tyr Val
     50                  55                  60

Gly Asn Val Trp Tyr Gln Arg Glu Val Phe Ile Pro Lys Gly Trp Ala
 65                  70                  75                  80

Gly Gln Arg Ile Val Leu Arg Phe Asp Ala Val Thr His Tyr Gly Lys
                 85                  90                  95

Val Trp Val Asn Asn Gln Glu Val His Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly His Val Ile Thr Asp Glu Asn Gly Lys Lys Lys Gln Ser Tyr
145                 150                 155                 160

Phe His Asp Phe Phe Asn Tyr Ala Gly Ile His Arg Ser Val His Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Gly Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Leu Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu His Val His Asp His Ala Leu His Asp Trp
305                 310                 315                 320

Ile Gly Ala Asn Ser Tyr Arg Thr Ser His Tyr Pro Tyr Ala Glu Glu
                325                 330                 335

His Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365
```

```
Asn Lys Pro Lys Glu Leu Tyr Ser Glu Ala Val Asn Gly Glu Thr
    370             375                 380

Gln Gln Ala His Leu Gln Ala Ile Lys Glu Leu Ile Ala Arg Asp Lys
385                 390                 395                 400

Asn His Pro Ser Val Val His Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val His Phe
            435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
                500                 505                 510

Leu His Ser His Tyr Thr Asp His Trp Ser Glu Glu Tyr Gln Cys Ala
            515                 520                 525

Trp Leu Asp His Tyr His Arg Val Phe Asp Arg Val Ser Ala Val Val
530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly His Asn
                580                 585                 590

Phe Gly Glu Lys Pro Gln Gln Gly Gly Lys Gln
                595                 600

<210> SEQ ID NO 2
<211> LENGTH: 613
<212> TYPE: PRT
<213> ORGANISM: Homo sapiens

<400> SEQUENCE: 2

Leu Gly Leu Gln Gly Gly His Leu Tyr Pro Gln Glu Ser Pro Ser Arg
1               5                   10                  15

Glu Cys Lys Glu Leu Asp Gly Leu Trp Ser Phe Arg Ala Asp Phe Ser
                20                  25                  30

Asp Asn Arg Arg Arg Gly Phe Glu Glu Gln Trp Tyr Arg Arg Pro Leu
            35                  40                  45

Trp Glu Ser Gly Pro Thr Val Asp His Pro Val Pro Ser Ser Phe Asn
50                  55                  60

Asp Ile Ser Gln Asp Trp Arg Leu Arg His Phe Val Gly Trp Val Trp
65                  70                  75                  80

Tyr Glu Arg Glu Val Ile Leu Pro Glu Arg Trp Thr Gln Asp Leu Arg
                85                  90                  95

Thr Arg Val Val Leu Arg Ile Gly Ser Ala His Ser Tyr Ala Ile Val
                100                 105                 110

Trp Val Asn Gly Val Asp Thr Leu Glu His Glu Gly Gly Tyr Leu Pro
            115                 120                 125

Phe Glu Ala Asp Ile Ser Asn Leu Val Gln Val Gly Pro Leu Pro Ser
130                 135                 140
```

```
Arg Leu Arg Ile Thr Ile Ala Ile Asn Asn Thr Leu Thr Pro Thr Thr
145                 150                 155                 160

Leu Pro Pro Gly Thr Ile Gln Tyr Leu Thr Asp Thr Ser Lys Tyr Pro
                165                 170                 175

Lys Gly Tyr Phe Val Gln Asn Thr Tyr Phe Asp Phe Asn Tyr Ala
            180                 185                 190

Gly Leu Gln Arg Ser Val Leu Leu Tyr Thr Thr Pro Thr Thr Tyr Ile
                195                 200                 205

Asp Asp Ile Thr Val Thr Thr Ser Val Glu Gln Asp Ser Gly Leu Val
210                 215                 220

Asn Tyr Gln Ile Ser Val Lys Gly Ser Asn Leu Phe Lys Leu Glu Val
225                 230                 235                 240

Arg Leu Leu Asp Ala Glu Asn Lys Val Val Ala Asn Gly Thr Gly Thr
                245                 250                 255

Gln Gly Gln Leu Lys Val Pro Gly Val Ser Leu Trp Trp Pro Tyr Leu
                260                 265                 270

His His Glu Arg Pro Ala Tyr Leu Tyr Ser Leu Glu Val Gln Leu Thr
                275                 280                 285

Ala Gln Thr Ser Leu Gly Pro Val Ser Asp Phe Tyr Thr Leu Pro Val
290                 295                 300

Gly Ile Arg Thr Val Ala Val Thr Lys Ser Gln Phe Leu Ile Asn Gly
305                 310                 315                 320

Lys Pro Phe Tyr Phe His Gly Val Asn Lys His Glu Asp Ala Asp Ile
                325                 330                 335

Arg Gly Lys Gly Phe Asp Trp Pro Leu Leu Val Lys Asp Phe Asn Leu
                340                 345                 350

Leu Arg Trp Leu Gly Ala Asn Ala Phe Arg Thr Ser His Tyr Pro Tyr
                355                 360                 365

Ala Glu Glu Val His Gln His Cys Asp Arg Tyr Gly Ile Val Val Ile
                370                 375                 380

Asp Glu Cys Pro Gly Val Gly Leu Ala Leu Pro Gln Phe Phe Asn Asn
385                 390                 395                 400

Val Ser Leu His His His His Gln Val His Glu Glu Val Val Arg Arg
                405                 410                 415

Asp Lys Asn His Pro Ala Val Val His Trp Ser Val Ala Asn Glu Pro
                420                 425                 430

Ala Ser His Leu Glu Ser Ala Gly Tyr Tyr Leu Lys His Val Ile Ala
                435                 440                 445

His Thr Lys Ser Leu Asp Pro Ser Arg Pro Val Thr Phe Val Ser Asn
                450                 455                 460

Ser Asn Tyr Ala Ala Asp Lys Gly Ala Pro Tyr Val Asp Val Ile Cys
465                 470                 475                 480

Leu Asn Ser Tyr Tyr Ser Trp Tyr His Asp Tyr Gly His Leu Glu Leu
                485                 490                 495

Ile Gln Leu Gln Leu Ala Thr Gln Phe Glu Asn Trp Tyr Lys Lys Tyr
                500                 505                 510

Gln Lys Pro Ile Ile Gln Ser Glu Tyr Gly Ala Glu Thr Ile Ala Gly
                515                 520                 525

Phe His Gln Asp Pro Pro Leu His Phe Thr Glu Glu Tyr Gln Lys Ser
                530                 535                 540

Leu Leu Glu Gln Tyr His Leu Gly Leu Asp Gln Lys Arg Arg Lys Tyr
545                 550                 555                 560
```

```
Val Val Gly Glu Leu Ile Trp Asn Phe Ala Asp Phe His Thr Glu Gln
            565                 570                 575

Ser Pro Thr Arg Val Leu Gly Asn Lys Lys Gly Ile Phe Thr Arg Gln
            580                 585                 590

Arg Gln Pro Lys Ser Ala Ala Phe Leu Leu Arg Glu Arg Tyr Trp Lys
        595                 600                 605

Ile Ala Asn Glu Thr
    610
```

SELECTIVE β-GLUCURONIDASE INHIBITORS AS A TREATMENT FOR SIDE EFFECTS OF CAMPTOTHECIN ANTINEOPLASTIC AGENTS

This application is a continuation of U.S. Ser. No. 13/514,418, filed Aug. 27, 2012, which is the U.S. National Stage of International Application No. PCT/US2010/059690, filed Dec. 9, 2010, which designates the U.S. and was published by the International Bureau in English on Jun. 16, 2011, and which claims the benefit of U.S. Provisional Patent Application No. 61/285,265, filed Dec. 10, 2009, and 61/408,032, filed Oct. 29, 2010; the contents of each of which are hereby incorporated herein in their entirety by reference.

GOVERNMENT SUPPORT

This invention was made with government support under Grant Number CA098468 awarded by the National Institutes of Health. The government has certain rights in the invention.

FIELD OF THE INVENTION

The invention relates generally to compositions and methods for inhibiting enteric bacterial enzymes and for attenuating side effects of antineoplastic agents, and more particularly to compositions and methods for inhibiting bacterial β-glucuronidases and for attenuating side effects of camptothecin-derived antineoplastic agents or glucuronidase-substrate agents or compounds used in the treatment of various neoplasms or other conditions.

BACKGROUND

Camptothecin, a plant alkaloid derived from the Chinese *Camptotheca acuminata* tree, was added to the National Cancer Institute's natural products screening set in 1966. It showed not only strong antineoplastic activity, but also poor bioavailability and toxic side effects. After thirty years of modifying the camptothecin scaffold, two camptothecin derivatives emerged and are now approved for clinical use. The first derivative is topotecan (also called Hycamptin®; GlaxoSmithKline; London, England), which can be used to treat solid brain, lung and ovarian tumors. The second derivative is irinotecan (also called CPT-11 and Camptosar®; Pfizer; New York City, N.Y.), which can be used to treat solid brain, colon and lung tumors, as well as refractory forms of leukemia and lymphoma.

The sole target of camptothecin and camptothecin-derived antineoplastic agents is human topoisomerase I. Camptothecin and camptothecin-derived antineoplastic agents bind to covalent topoisomerase I-DNA complexes and prevent re-ligation of broken single DNA strands, effectively trapping it on the DNA. Such immobilized macromolecular adducts act as roadblocks to the progression of DNA replication and transcription complexes, causing double-strand DNA breaks and apoptosis. Structural studies have established that camptothecin and other camptothecin-derived antineoplastic agents stack into duplex DNA, replacing the base pair adjacent to the covalent phosphotyrosine linkage. See, Chrencik et al. (2004) *J. Mol. Biol.* 339:773-784; and Staker et al (2002) *Proc. Natl. Acad. Set. USA* 99:15387-15392. Re-ligation of the nicked DNA strand is prevented by increasing the distance between the 5'-hydroxyl and the 3'-phosphotyrosine linkage to >11 Å. Because neoplastic cells grow rapidly, camptothecin and other camptothecin-derived antineoplastic agents impact these cells more significantly than normal cells and tissues.

Camptothecin-derived antineoplastic agent efficacy, including that of camptothecin, is limited by a delayed diarrhea that follows its administration by about two to four days. For example, "reactivation" of SN-38G, a glucuronidated inactive metabolite of irinotecan, to SN-38, its active metabolite, by β-glucuronidases of enteric bacteria kills intestinal epithelial cells and causes a dose-limiting diarrhea. See, e.g., Matsui et al. (2003) *Surg. Oncol. Clin. N. Am.* 12:795-811; and Tobin et al. (2003) *Oncol. Rep.* 10:1977-1979.

While broad-spectrum antibiotics have been used to eliminate enteric bacteria from the gastrointestinal tract prior to irinotecan treatment to reduce reactivation, this approach has several drawbacks. First, enteric bacteria (i.e., normal flora) play essential roles in carbohydrate metabolism, vitamin production and the processing of bile acids, sterols and xenobiotics. Thus, a partial or complete removal of enteric bacteria is not ideal for subjects already challenged by neoplastic growths and chemotherapy. Second, the elimination of the symbiotic enteric bacteria from even healthy subjects significantly increases risk of infection by pathogenic bacteria, including enterohemorrhagic *Escherichia coli* and *Clostridium difficile*. Third, bacterial antibiotic resistance is a human health crisis, and the unnecessary use of antibiotics is a significant contributor to this crisis.

Likewise, weak/non-selective β-glucuronidase inhibitors such as saccharic acid 1,4-lactone can be administered to reduce reactivation. These inhibitors, however, are only partially effective in preventing reactivation of glucuronidated metabolites of camptothecin and other camptothecin-derived antineoplastic agents. Fittkau et al. (2004) *J. Cancer Res. Clin. Oncol.* 130:388-394. Additional non-specific inhibitors of β-glucuronidase include certain divalent cations (e.g., $Cu^{2+}$ and $Zn^{2+}$), galacturonic acid and glucuronic acid. Naleway, "Histochemical, spectrophotometric, and fluorometric GUS substrates" 61-76 In: GUS Protocols: Using the GUS Gene as a Reporter of Gene Expression (Gallagher ed., Academic Press 1992); and Handbook of Enzyme Inhibitors, Part A (Zollner ed., $2^{nd}$ ed. 1993).

For the foregoing reasons, there is a need for alternative compositions and methods for inhibiting bacterial β-glucuronidases and for attenuating reactivation of glucuronidated metabolites of camptothecin and other camptothecin-derived antineoplastic agents or any other glucuronidase-substrate agents or compounds.

BRIEF SUMMARY

Compositions and methods are provided for selectively inhibiting bacterial β-glucuronidases. Accordingly, compositions of the present invention include β-glucuronidase inhibiting agents that selectively inhibit bacterial β-glucuronidases from hydrolyzing glucuronides. The selectively inhibiting agents can be provided as formulated compositions and can be administered to subjects in need thereof. In particular, the selectively inhibiting agents or compositions comprising such agents can be administered prior to, concurrently with or after an antineoplastic agent, particularly a camptothecin-derived antineoplastic agent, to treat a variety of neoplasms including cancers, or in the same manner can be used with any other glucuronidase-substrate agent(s) or compound(s). When used together, the selectively inhibiting agent reduces side effects of antineoplastic agents or any other glucuronidase-substrate agent(s) or compound(s), thus improving efficacy of the antineoplastic agent or other agents.

The selectively inhibiting agents and compositions can be used in methods for treating cancer and for reducing side effects of antineoplastic agents, such as camptothecin-derived antineoplastic agents. Thus, the gastrointestinal distress that typically accompanies treatment with an antineoplastic agent can be attenuated. The methods are also useful for attenuating or improving any adverse reactions associated with administration of glucuronidase-substrate agent(s) or compound(s).

Methods of the present invention include administering to a subject in need thereof a therapeutically effective amount of at least one β-glucuronidase inhibiting agent that selectively inhibits bacterial β-glucuronidases from hydrolyzing glucuronides.

The present invention provides the first potent, selective inhibitors of bacterial β-glucuronidases in both aerobic and anaerobic bacteria associated with the gastrointestinal tract.

The following embodiments are encompassed by the present invention.

1. A compound having selective β-glucuronidase inhibitor activity, the compound selected from the group consisting of:

(1)
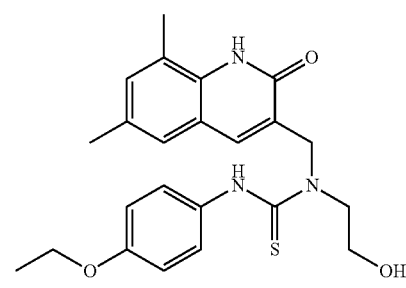

(2)
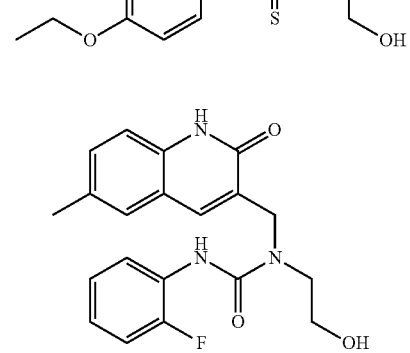

(3)
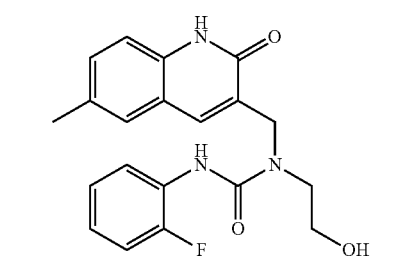

(4)
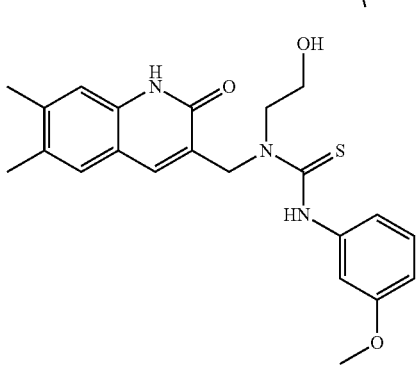

-continued (5)
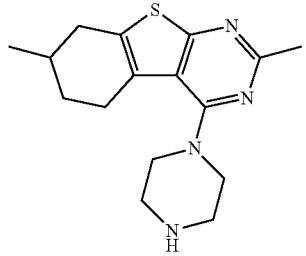

(6)
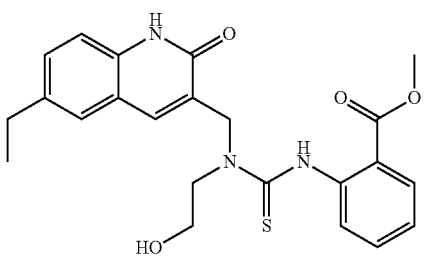

(7)
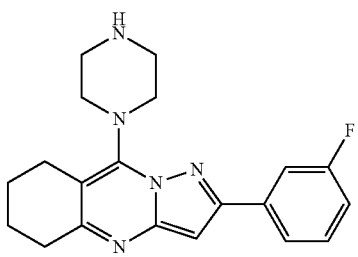

(8)
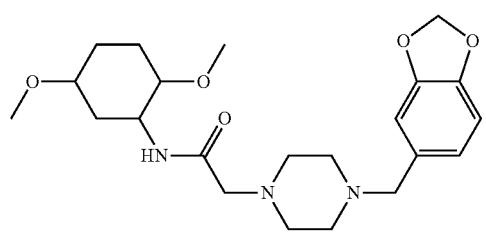

(9)
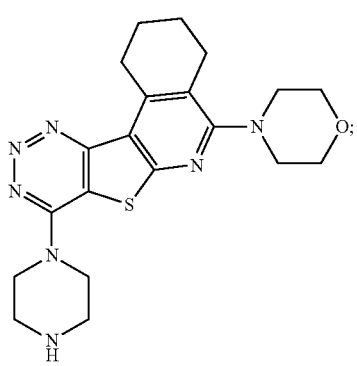

and active derivatives thereof.

2. A composition comprising at least one compound selected from the group consisting of the compounds of embodiment 1.

3. The composition of embodiment 2 further comprising a pharmaceutically acceptable carrier.

4. The composition of embodiment 2 or 3 wherein said composition is administered prior to, concurrently with, or after the administration of at least one camptothecin-derived antineoplastic agent 5. The composition of embodiment 4, wherein at least one camptothecin-derived antineoplastic agent is selected from the group consisting of camptothecin, diflomotecan, exatecan, gimatecan, irinotecan, karenitecin, lurtotecan, rubitecan, silatecan and topotecan.

6. The composition of any of embodiments 2-5, wherein the at least one selective β-glucuronidase inhibitor is at a concentration from about 1 nM to about 1 mM.

7. A method for selectively inhibiting bacterial β-glucuronidases, the method comprising administering to a subject in need thereof an effective amount of at least one selective β-glucuronidase inhibitor.

8. The method of embodiment 7, wherein the at least one selective β-glucuronidase inhibitor is selected from the compounds of embodiment 1.

9. The method of embodiment 8, wherein the at least one selective β-glucuronidase inhibitor is administered to the subject at a concentration from about 1 nM to about 1 mM.

10. The method of embodiment 7, wherein the bacterial β-glucuronidases are enteric bacterial β-glucuronidases.

11. The method of embodiment 10, wherein the bacteria are selected from the group consisting of a *Bacteroides* sp., *Bifidobacterium* sp., *Catenabacterium* sp., *Clostridium* sp., *Corynebacterium* sp., *Enterococcus faecalis*, Enterobacteriaceae, *Lactobacillus* sp., *Peptostreptococcus* sp., *Propionibacterium* sp., *Proteus* sp., *Mycobacterium* sp., *Pseudomonas* sp., *Staphylococcus* sp. and *Streptococcus* sp.

12. A method for improving camptothecin-derived antineoplastic agent efficiency, the method comprising administering to a subject prior to, concurrently with or after administration of a camptothecin-derived antineoplastic agent a therapeutically effective amount of at least one selective β-glucuronidase inhibitor.

13. A method for attenuating side effects in a subject being administered a camptothecin-derived antineoplastic agent, the method comprising administering prior to, concurrently with or after administration of a camptothecin-derived antineoplastic agent a therapeutically effective amount of at least one selective 3-glucuronidase inhibitor.

14. The method of embodiment 12 or 13, wherein the at least one selective β-glucuronidase inhibitor is selected from the compounds of embodiment 1.

15. The method of embodiment 12 or 13, wherein the camptothecin-derived antineoplastic agent is selected from the group consisting of camptothecin, diflomotecan, exatecan, gimatecan, irinotecan, karenitecin, lurtotecan, rubitecan, silatecan and topotecan.

16. The method of embodiment 15, wherein the camptothecin-derived antineoplastic agent is irinotecan.

17. A method to alleviate gastrointestinal distress associated with chemotherapy comprising:
a) administering to an animal an anti-cancer effective amount of a chemotherapeutic agent, and
b) administering to the same animal an inhibitory effective amount of a β-glucuronidase inhibitor.

18. The method of embodiment 17, wherein the chemotherapeutic active agent is a camptothecin-derived antineoplastic agent.

19. The method of embodiment 17, wherein the 3-glucuronidase inhibitor is selected from the group consisting of:

(1)
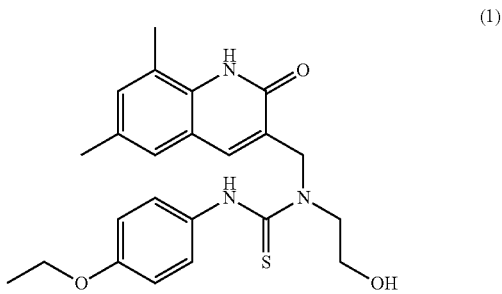

(2)
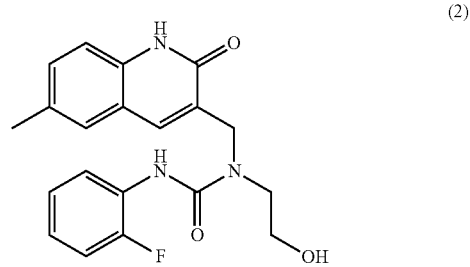

(3)
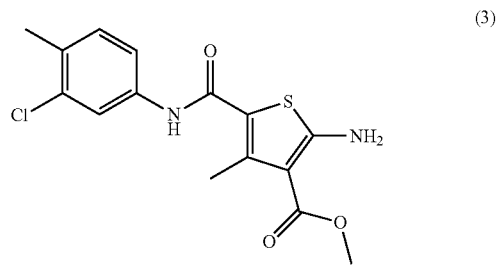

(4)
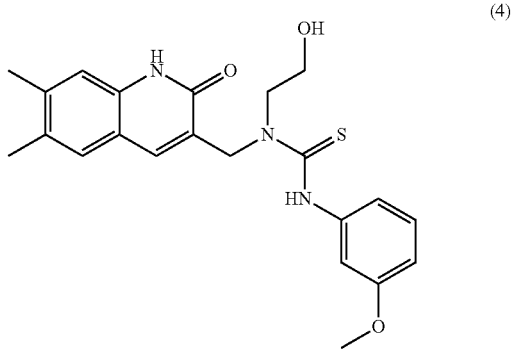

(5)
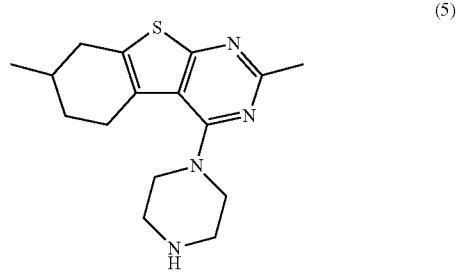

(6)
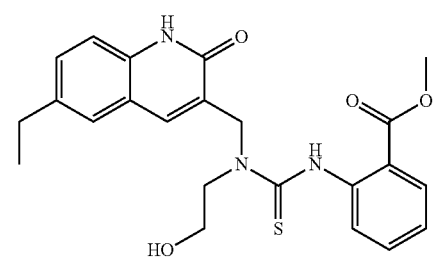

(7)
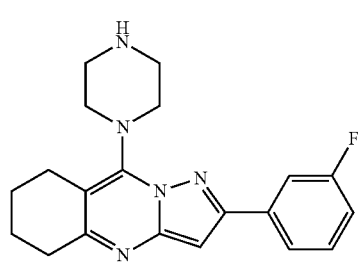

(8)
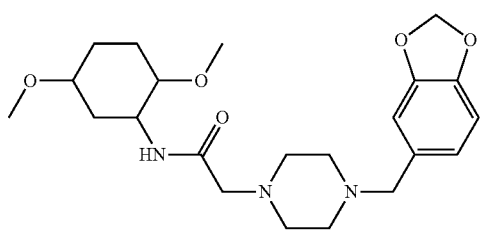

(9)
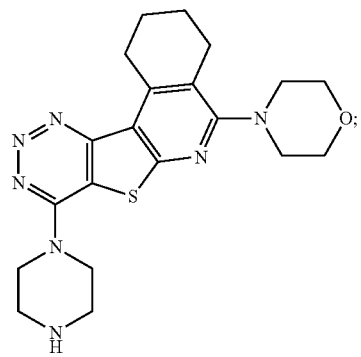

and active derivatives thereof.

20. A method for improving the efficiency of a glucuronidase-substrate agent or compound, the method comprising administering to a subject prior to, concurrently with or after administration of said agent or compound a therapeutically effective amount of at least one selective β-glucuronidase inhibitor.

21. The method of embodiment 20, wherein said selective β-glucuronidase inhibitor is selected from the group consisting of:

(1)
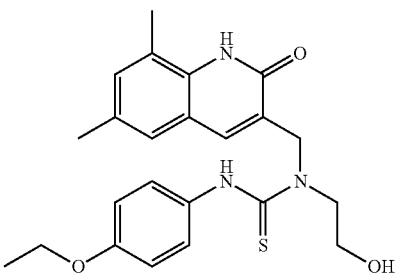

(2)
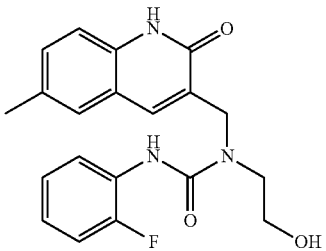

(3)
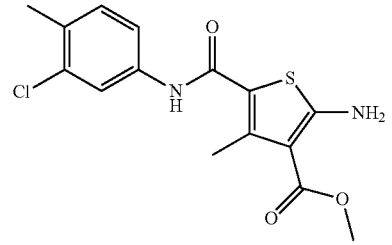

(4)
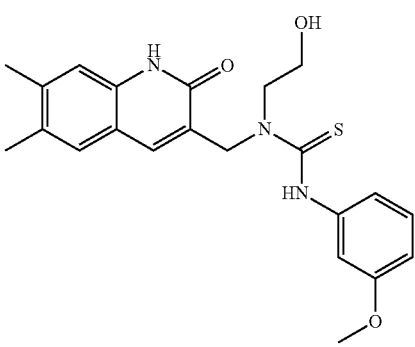

(5)
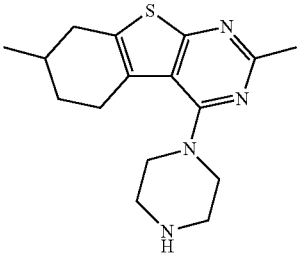

(6)
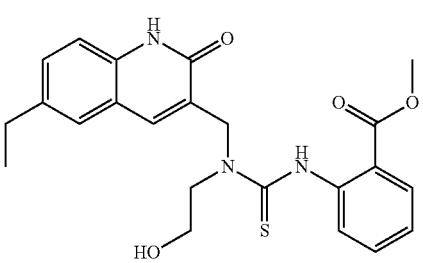

-continued

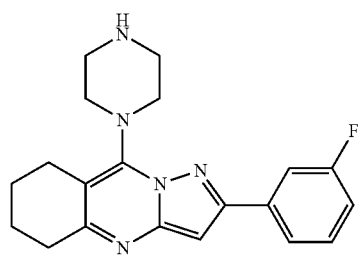
(7)

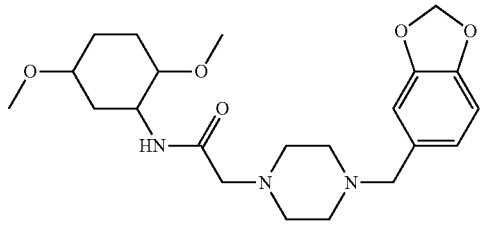
(8)

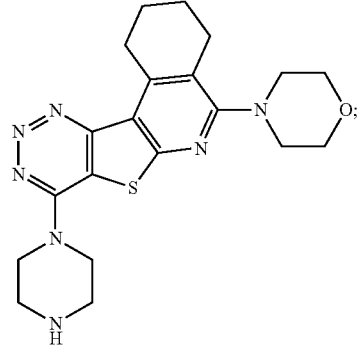
(9)

and active derivatives thereof.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1A:
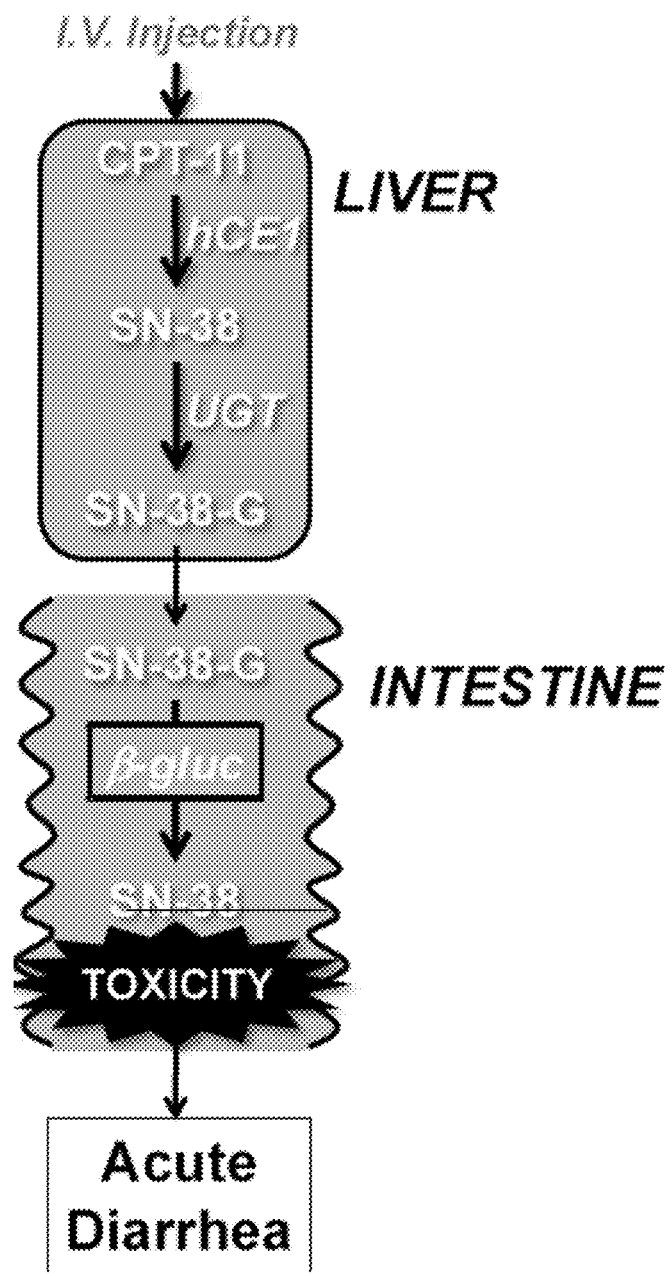
FIG. 1A shows a diagram of the activation and metabolism of irinotecan.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

Overview

The present invention relates to an identification of potent (i.e., low uM to high pM), selective β-glucuronidase inhibitors for both aerobic and anaerobic bacteria, especially those bacteria associated with the gastrointestinal tract (i.e., enteric bacteria). The present invention therefore includes compositions and methods for inhibiting bacterial β-glucuronidases and for improving efficacy of camptothecin-derived antineoplastic agents or glucuronidase-substrate agents or compounds by attenuating the gastrointestinal distress caused by reactivation of glucuronidated metabolites of such agents.

Compounds of interest herein include:

(1)
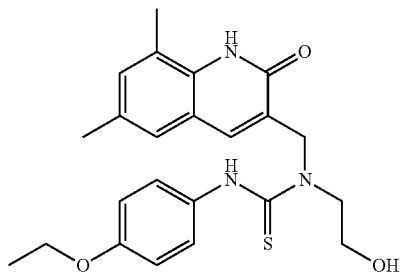

(2)
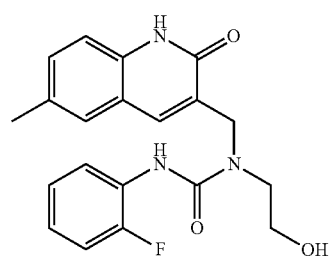

(3)
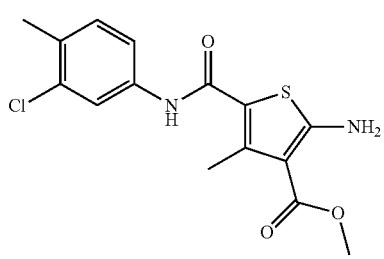

(4)
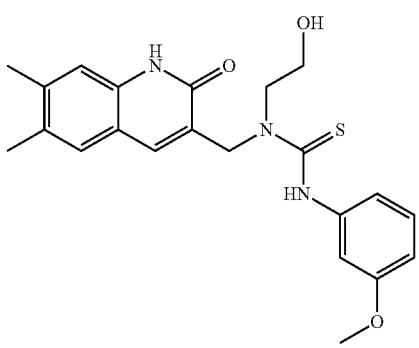

(5)
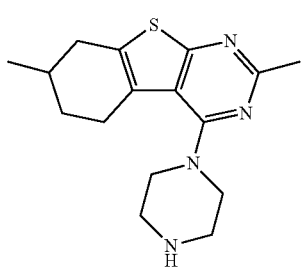

(6)
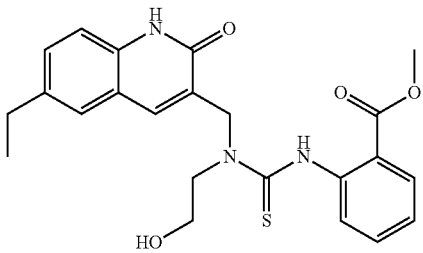

(7)
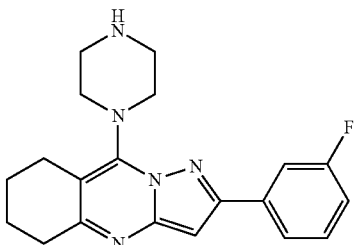

(8)
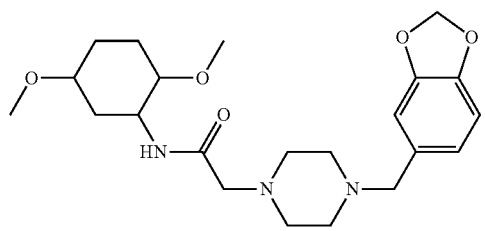

(9)
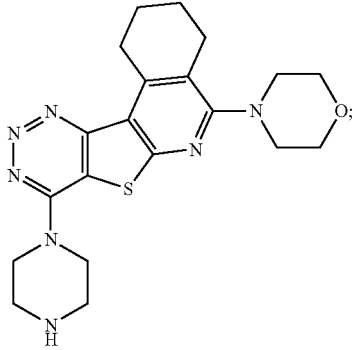

and active derivatives thereof.

As used herein, "active derivative" and the like means a modified β-glucuronidase inhibiting compound that retains an ability to selectively inhibit bacterial β-glucuronidases. For example, the derivative can be capable of inhibiting β-glucuronidase reactivation of SN-38G to SN-38, but not killing bacteria that inhabit the gastrointestinal tract or inhibiting mammalian β-glucuronidases. One of skill in the art is familiar with assays for testing the ability of an active derivative compound for selectively inhibiting β-glucuronidases with no toxicity to the bacteria that inhabit the gastrointestinal tract. See, Experimental section below.

As used herein, "inhibit," "inhibiting" and the like means that β-glucuronidase expression, activity or function and therefore metabolite reactivation can be reduced in a subject. Likewise, "attenuate" means to reduce or lessen. That is, the β-glucuronidase activity can be reduced. Likewise, the side effects of a chemotherapeutic agent can be reduced. Thus, to inhibit or attenuate means a reduction of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or up to about 100% as compared to an appropriate control.

As used herein, "selectively inhibit" and the like means that a β-glucuronidase inhibitor reduces bacterial, but not mammalian, β-glucuronidase activity. That is, the β-glucuronidase inhibitor can bind to and can prevent bacterial, but not mammalian, β-glucuronidases from hydrolyzing glucuronides.

As used herein, "β-glucuronidase" and the like means an enzyme (EC 3.2.1.31) capable of hydrolyzing β-glucuronides, but not β-glucuronides or β-glucosides. See, Basinska & Florianczyk (2003) *Ann. Univ. Mariae Curie Sklodowska Med.* 58:386-389; Miles et al. (1955) *J. Biol. Chem.* 217:921-930. As used herein, a "glucuronide" and the like means a substance produced by linking glucuronic acid to another substance via a glycosidic bond. Examples of glucuronides of interest herein include, but are not limited to, glucuronides of camptothecin-derived antineoplastic agents such as SN-38G (7-ethyl-10-hydroxycamptothecin glucuronide).

As used herein, "camptothecin-derived antineoplastic agent" and the like means a cytotoxic quinoline alkaloid that inhibits the DNA enzyme topoisomerase I. A camptothecin-derived antineoplastic agent can include a structure comprising at least the following:

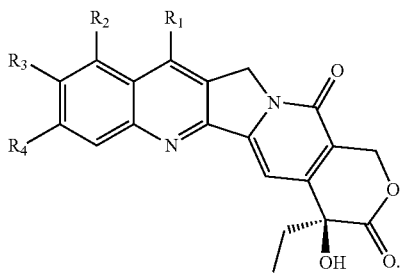

Camptothecin-derived antineoplastic agents include, but are not limited to, camptothecin (i.e., (S)-4-ethyl-4-hydroxy-1H-pyrano[3',4'6,7]indolizino[1,2-b]quinoline-3,14-(4H,12H)-dione); diflomotecan (i.e., (5R)-5-ethyl-9,10-difluoro-1,4,5,13-tetrahydro-5-hydroxy-3H,15H-oxepino[3',':6,7]indolizino[1,2-b]quinoline-3,15-dione); exatecan (i.e., (1S,9S)-1-amino-9-ethyl-5-fluoro-1,2,3,9,12,15-hexahydro-9-hydroxy-4-methyl-10H,13H-benzo(de)pyrano(3',4':6,7)indolizino(1,2-b)quinoline-10,13-dione); gimatecan (i.e., (4S)-11-((E)-((1,1-dimethylethoxy)imino)methyl)-4-ethyl-4-hydroxy-1,12-dihydro-14H-pyrano(3',4',6,7)indolizino(1,2-b)quinoline-3,14(4H)-dione); irinotecan (i.e., (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate); karenitecin (i.e., (4S)-4-ethyl-4-hydroxy-11-(2-trimethylsilyl)ethyl)-1H-pyrano[3',4':6,7]indolizino[1,2-b]quinoline-3,14(4H,12H)-dione); lurtotecan (i.e., 7-(4-methylpiperazinomethylene)-10,11-ethylenedioxy-20(S)-camptothecin); rubitecan (i.e., (4S)-4-ethyl-4-hydroxy-10-nitro-1H-pyrano[3,4':6,7]indolizino[1,2-b]quinoline-3,14(4H,12H)-dione); silatecan (i.e., 7-tert-butyldimethylsilyl-10-hydroxycamptothecin); and topotecan (i.e., (S)-10-[(dimethylamino)methyl]-4-ethyl-4,9-dihydroxy-1H-pyrano[3',4':6,7]indolizino[1,2-b]quinoline-3,14 (4H,12H)-dione).

Of interest herein is irinotecan (CPT-11 or Camptosan®), which is a potent camptothecin-derived antineoplastic agent for treating solid malignancies of the brain, colon and lung, as well as refractory forms of leukemia and lymphoma. Irinotecan is a prodrug that must be converted into its active form, SN-38 (7-ethyl-10-hydroxycamptothecin), to have antineoplastic activity. During its excretion, SN-38 is glucuronidated to SN-38 glucuronide (SN-38G) by phase II drug metabolizing UDP-glucuronosyltransferases.

The term "glucuronidase-substrate agent(s) or compound(s)" refers to any drug, agent or compound or, in particular, a metabolite thereof that can be a substrate for glucuronidase. Thus, in some instances, a drug, compound or agent that is not itself a substrate, but is metabolized to a substrate is encompassed by the term as used herein. Any drug, compound or agent or metabolite thereof that is glucuronidated, also referred to as glucuronides, can be a substrate for glucuronidase and is also described herein as glucuronidase-substrate agent(s) or compound(s). Many drugs, agents or compounds undergo glucuronidation at some point in their metabolism. Alternatively, the drug, agent or compound may be a glucuronide pro-drug. These glucuronides may have different properties than the parent drug, agent or compound. Glucuronidation can modulate the potency of some drugs: the 6-glucuronide of morphine is a more potent analgesic than the parent compound, whereas the 3-glucuronide is a morphine antagonist. In addition, steroid glucuronidation can produce more active or toxic metabolites under pathophysiological conditions or during steroid therapies.

Drugs, agents or compounds or metabolites thereof which are substrates for glucuronidase can have their respective properties altered by glucuronidase hydrolysis. In a specific, non-limiting example, if the drug, agent, compound or metabolite thereof has been metabolized to a glucuronide, the hydrolysis of the glucuronide can reactivate the drug, agent, compound or metabolite thereof. In many cases, this reactivation can cause adverse reactions. For example, if a glucuronide drug, agent or compound or metabolite thereof is present in the gut, glucuronidase hydrolysis in the gut can lead to gastrointestinal distress.

The methods described herein are useful for attenuating, ameliorating or improving the adverse reactions, such as gastrointestinal distress, caused by the action of glucuronidase on a drug, agent or compound or, in particular, a metabolite thereof. As described fully elsewhere herein, hydrolysis of glucuronides can lead to adverse reactions. The methods described herein inhibit or decrease the activity of β-glucuronidases. The methods can therefore be useful to attenuate, ameliorate or improve adverse reactions, such as gastrointestinal distress, associated with administering such drugs, agents or compounds. The methods can also improve the tolerance of any such drug, agent or compound or metabolite thereof that can form a glucuronide. As such, administration of a glucuronidase inhibitor can rescue or improve a treatment with any drug, agent or compound, wherein glucuronidase hydrolysis of a glucuronide related to the drug, agent, compound or metabolite thereof is causing one or more adverse reactions, particularly gastrointestinal distress or toxicity. Patient compliance and outlook would also improve with the lessening of adverse reactions.

Reactivation of inactive metabolites such as SN-38G to active SN-38 occurs in the gastrointestinal tract and results from bacterial β-glucuronidases. As noted above, the reactivated metabolites can lead to a gastrointestinal distress such as diarrhea, which often can be a dose-limiting side effect of the cancer therapy or the therapy to treat any other conditions. As used herein, "dose-limiting" indicates that the side effect from administration of a camptothecin-derived antineoplastic agent or glucuronidase-substrate agents or compounds prevents a subject in need of cancer therapy or therapy to treat any other conditions from receiving a recommended amount. As increasing amounts of the camptothecin-derived antineoplastic agent or glucuronidase-substrate agents or compounds are administered to a subject, increased amounts of glucuronidated metabolites are therefore available as a substrate for the bacterial β-glucuronidases. The resulting reactivated metabolites not only adversely affect a subject's well-being by causing serious side effects, particularly gastrointestinal distress, but also impair treatment outcome by limiting the amount of the camptothecin-derived antineoplastic agent or glucuronidase-substrate agents or compounds that can be administered to the subject.

The selective β-glucuronidase inhibiting compounds, compositions, and methods of use thereof described herein are useful in a variety of applications. For example, the compounds, compositions and methods disclosed herein can be used for discovering additional selective β-glucuronidase inhibitors in a screening assay as controls in which potential selective β-glucuronidase inhibitors can be compared.

The selective β-glucuronidase inhibiting compounds, compositions and methods of use thereof also can be used to improve efficacy of camptothecin-derived antineoplastic agents or glucuronidase-substrate agents or compounds by attenuating the side effects associated with their administration during the treatment of various neoplasms or other conditions. As used herein, "neoplasm" and the like means an abnormal growth of cells or a mass of tissue resulting from an abnormal proliferation of cells. Neoplasms frequently result in a lump or tumor and can be benign, pre-malignant (i.e., pre-cancerous) or malignant (i.e., cancerous growths including primary or metastatic cancerous growths). "Neoplastic" means of or related to a neoplasm. Thus, the selective β-glucuronidase inhibiting compounds and compositions can be used to improve treatment of a variety of neoplasms including, but not limited to, neoplasms of the bone, brain, breast, cervix, colon, intestines, kidney, liver, lung, pancreatic, prostate, rectum, stomach, throat, uterus, and the like. The term "conditions" refers to any disease or disorder for which the glucuronidase-substrate agents or compounds are being primarily administered.

Compositions

The present invention provides compounds and compositions for selectively inhibiting bacterial β-glucuronidases. The compounds and compositions can include an effective amount of at least one selective β-glucuronidase inhibitor selected from the inhibitors described herein. As used herein, "effective amount" and the like means that amount of an inhibitor or other therapeutic agent that will elicit a biological or medical response of a cell, tissue, system or animal that is being sought, for instance, by a researcher or clinician. That is, the effective amount of a selective β-glucuronidase inhibitor or composition thereof is an amount sufficient to reduce or attenuate side effects of camptothecin-derived antineoplastic agents or glucuronidase-substrate agents or compounds. Particularly, the effective amount is that amount of the selective β-glucuronidase inhibitor or composition thereof to attenuate the side effects in a subjected being treated with a camptothecin-derived antineoplastic agent or glucuronidase-substrate agents or compounds. More particularly, the effective amount is that amount sufficient to inhibit reactivation of glucuronidated metabolites such as SN-38G to SN-38. For example, the effective amount of the selective β-glucuronidase inhibitor can be about 1 pM to about 1 mM, about 1 nM to about 1 mM, about 1 M to about 1 mM, about 1 mM to about 1 nM, about 1 nM to about 1 µM, or about 1 µM to about 1 mM.

As used herein, "about" means within a statistically meaningful range of a value such as a stated concentration range, time frame, molecular weight, volume, temperature or pH. Such a range can be within an order of magnitude, typically within 20%, more typically still within 10%, and even more typically within 5% of a given value or range. The allowable variation encompassed by "about" will depend upon the particular system under study, and can be readily appreciated by one of skill in the art.

Examples of selective β-glucuronidase inhibitors include, but are not limited to,

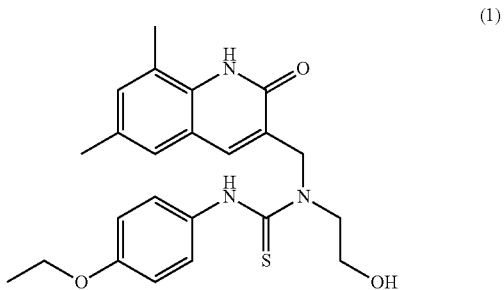

(1)

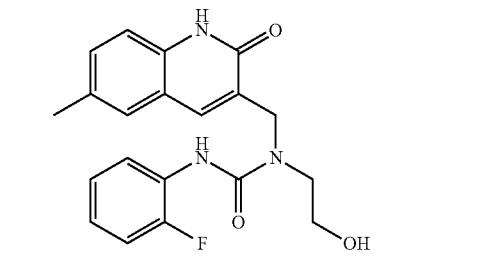

(2)

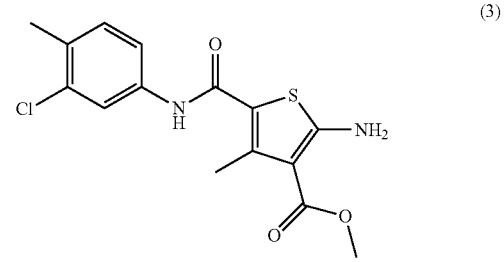

(3)

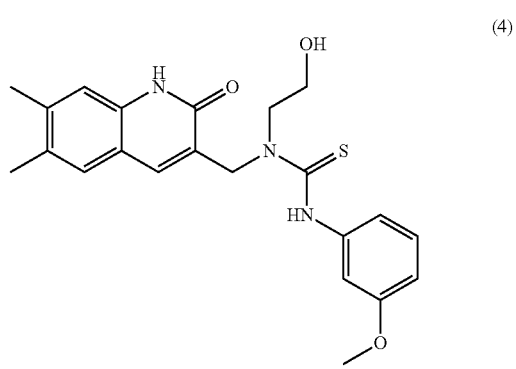

(4)

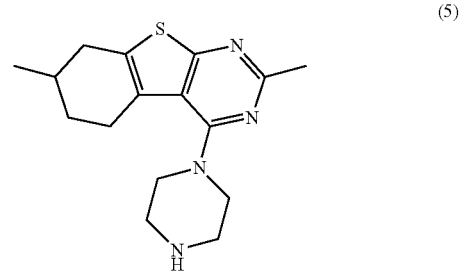

(5)

(6)
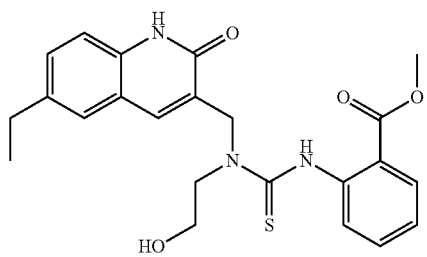

(7)
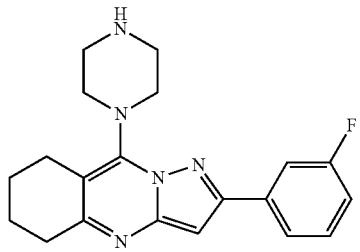

(8)
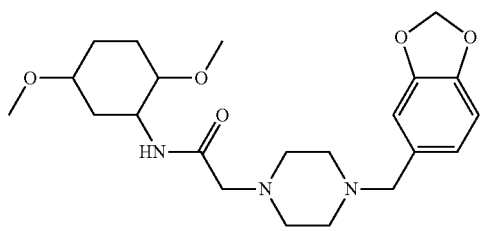

(9)
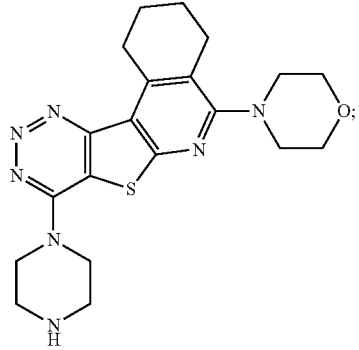

and active derivatives thereof.

Advantageously, the β-glucuronidase inhibitors described herein are selective for bacterial β-glucuronidases. That is, the compounds inhibit β-glucuronidase in bacteria but do not have inhibitory activity toward mammalian β-glucuronidases, including human β-glucuronidase. While not intending to be bound by any particular mechanism of action, the compounds appear to bind a ~12 residue loop in bacterial β-glucuronidases that hovers over an active site opening. The loop is not present in mammalian β-glucuronidases, which therefore can accommodate larger substrates and cleave glucuronic acid moieties from long-chain glycosaminoglycans.

The β-glucuronidase inhibitors exhibit other advantages. For example, the compounds do not kill the enteric bacteria or harm human epithelial cells, but are effective against bacteria cultured under aerobic and anaerobic conditions.

The present invention also provides compositions comprising the selective β-glucuronidase inhibitors. The compositions can include at least one selective β-glucuronidase inhibitor selected from the inhibitors described herein and a pharmaceutically acceptable carrier. The compositions are formulated to administer an effective amount to a subject in need thereof.

As used herein, "pharmaceutically acceptable" or "pharmacologically acceptable" means a material that is not biologically, physiologically or otherwise undesirable to a subject, i.e., the material may be administered to the subject in a formulation or composition without causing any undesirable biological effects or interacting in a deleterious manner with any of the components of the composition in which it is contained.

The pharmaceutically acceptable carrier can be a solid or liquid and the type can be generally chosen based on the type of administration being used. The selective β-glucuronidase inhibitor can be administered in the form of a tablet or capsule, as an agglomerated powder or in a liquid form. Examples of solid carriers include, but are not limited to, lactose, sucrose, gelatin and agar. Capsule or tablets can be easily formulated and can be made easy to swallow or chew; other solid forms include granules, and bulk powders. Tablets can contain suitable binders, lubricants, diluents, disintegrating agents, coloring agents, flavoring agents, flow-inducing agents, and melting agents.

Examples of liquid dosage forms include solutions or suspensions in water, pharmaceutically acceptable fats or oils, alcohols or other organic solvents, including esters, emulsion, elixirs, syrups, solutions and/or suspensions reconstituted from non-effervescent granules and effervescent preparations reconstituted from effervescent granules. Such liquid dosage forms can contain, e.g., suitable solvents, preservatives, emulsifying agents, suspending agents, diluents, sweeteners, thickeners and melting agents. Oral dosage forms can contain flavorants and coloring agents.

The compositions of the invention also can include minerals and/or vitamins such as, calcium, vitamin A, vitamin B, vitamin D and vitamin E.

Methods

The present invention provides methods for selectively inhibiting bacterial β-glucuronidases. In the methods, an effective amount of at least one selective β-glucuronidase inhibitor can be administered to a subject in need thereof. That is, a subject being treated with a camptothecin-derived antineoplastic agent or glucuronidase-substrate agents or compounds.

As used herein, "enteric bacteria" and the like mean the normal bacteria that inhabit the human gastrointestinal track. Examples of enteric bacteria include, but are not limited to, *Bacteroides* sp. (e.g., *Bateroides vulgatus*), *Bifidobacterium* sp. (e.g., *Bifidobacterium bifidum* and *Bifidobacterium infantis*), *Catenabacterium* sp., *Clostridium* sp., *Corynebacterium* sp., *Enterococcus* sp. (e.g., *Enterococcus faecalis*), Enterobacteriaceae (e.g., *Escherichia coli*), *Lactobacillus* sp., *Peptostreptococcus* sp., *Propionibacterium* sp., *Proteus* sp., *Mycobacterium* sp., *Pseudomonas* sp. (e.g., *Pseudomonas aeruginosa*), *Staphylococcus* sp. (e.g., *Staphylococcus epidermidis* and *Staphylococcus aureus*) and *Streptococcus* sp. (e.g., *Streptococcus mitts*). Because enteric bacteria commensally inhabit the gastrointestinal tract, they promote gastrointestinal health by preventing infection by opportunistic bacteria like *Clostridum difficle*.

Methods for assessing β-glucuronidase activity are known in the art. See, e.g., Farnleitner et al. (2002) *Water Res.* 36:975-981; Fior et al. (2009) *Plant Sci.* 176:130-135; and Szasz (1967) *Clin. Chem.* 13:752-759. β-glucuronidase activity of bacteria provided the selective β-glucuronidase inhibitor can be reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% when compared to bacteria not provided the selective β-glucuronidase inhibitor.

The present invention also provides methods for improving efficacy of camptothecin-derived antineoplastic agents or glucuronidase-substrate agents or compounds by attenuating reactivation by bacterial β-glucuronidases of glucuronidated metabolites of camptothecin-derived antineoplastic agents or glucuronidase-substrate agents or compounds. In the methods, a therapeutically effective amount of at least one selective β-glucuronidase inhibitor can be administered to a subject having or about to have treatment with a chemotherapeutic agent, particularly a camptothecin-derived antineoplastic agent or any other glucuronidase-substrate agents or compounds.

As used herein, "subject" means a mammal including but not limited to a cat, dog, horse, mouse, rat, non-human primate and human, but preferably a human.

The therapeutically effective amount of the at least one selective β-glucuronidase inhibitor can be administered to the subject prior to, concurrently with or after administration of a camptothecin-derived antineoplastic agent or glucuronidase-substrate agent or compound. When the selective β-glucuronidase inhibitor is administered prior to the camptothecin-derived antineoplastic agent or glucuronidase-substrate agent or compound, it can be as a prophylactic measure. For example, the selective β-glucuronidase inhibitor can be provided about 2 weeks, 1 week, 6 days, 5 days, 4 days, 3 days, 2 days, 1 day, 12 hours, 10 hours, 8 hours, 6 hours, 5 hours, 4 hours, 3 hours, 2 hours, 1 hour or even 30 minutes prior to or after the camptothecin-derived antineoplastic agent or glucuronidase-substrate agent or compound.

The compounds and compositions are generally administered via an oral route. However, any route of administration that will provide the compounds to the intestine can be used.

One of skill in the art understands that the effective amount provided to a subject in need thereof can and will vary depending upon several clinical parameters. For example, the therapeutically effective amount of the selective β-glucuronidase inhibitor will depend on the subject being treated (e.g., age, weight, sex, etc.), the severity of the disorder or disease, and the route of administration. Likewise, the therapeutically effective amount will vary depending upon clinical and treatment parameters.

In an embodiment, the subject matter described herein is directed to the use of a selective β-glucuronidase inhibitor for the manufacture of a medicament for the use in selectively inhibiting bacterial β-glucuronidases, for improving camptothecin-derived antineoplastic agent efficiency, for attenuating side effects in a subject being administered a camptothecin-derived antineoplastic agent, for alleviating gastrointestinal distress associated with chemotherapy, and for improving the efficiency of a glucuronidase-substrate agent or compound.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

The following examples are offered by way of illustration and not by way of limitation.

EXPERIMENTAL

Camptothecin, a plant alkaloid derived from the Chinese *Camptotheca acuminata* tree, was added to the NCI natural products screening set in 1966. It showed strong antineoplastic activity but poor bioavailability and toxic side effects. After thirty years of modifying the camptothecin scaffold, two derivatives emerged and are now approved for clinical use. (Pizzolato & Saltz (2003). *Lancet* 361:2235-2242). Topotecan (Hycamptin®; GlaxoSmithKline) is currently employed to treat solid ovarian, lung and brain tumors. Id. CPT-11 (also called Irinotecan, and Camptosar®; Pfizer) contains a carbamate-linked dipiperidino moiety that significantly increases bioavailability in mammals. Id. This dipiperidino group is removed from the CPT-11 prodrug in vivo by carboxylesterase enzymes that hydrolyze the carbamate linkage to produce the drug's active metabolite, SN-38. (Smith et al. (2006) *Toxicol In Vitro* 20:163-175). CPT-11 is currently used to treat solid colon, lung and brain tumors, along with refractory forms of leukemia and lymphoma. (Pommier (2006) *Nat Rev Cancer* 6:789-802).

The sole target of the camptothecins is human topoisomerase I. (Hsiang et al. (1985) *J Biol Chem* 260:14873-14878). This enzyme relieves superhelical tension throughout the genome and is essential for DNA metabolism, including DNA replication, transcription and homologous recombination. (Redinbo et al. (1999) *Curr Opin Struct Biol* 9:29-36). Topoisomerase I breaks one strand in duplex DNA, forming a covalent 3'-phosphotyrosine linkage, and guides the relaxation of DNA supercoils. (Redinbo et al. (1998) *Science* 279:1504-1513; Stewart et al. (1998) *Science* 279: 1534-1541). It then reseals the single-strand DNA break and releases a relaxed duplex DNA molecule. The camptothecins bind to the covalent topoisomerase I-DNA complex and prevent the religation of the broken single DNA strand, effectively trapping the 91 kDa protein on the DNA. (Hsiang, 1985). Such immobilized macromolecular adducts act as roadblocks to the progression of DNA replication and transcription complexes, causing double-strand DNA breaks and apoptosis. (Pommier, 2006). Because cancer cells are growing rapidly, the camptothecins impact neoplastic cells more significantly than normal human tissues. Structural studies have established that the camptothecins stack into the duplex DNA, replacing the base pair adjacent to the covalent phosphotyrosine linkage. (Chrencik et al. (2004) *J Mol Biol* 339: 773-784; Staker et al. (2002) *Proc Natl Acad Sci USA* 99:15387-15392). Religation of the nicked DNA strand is prevented by increasing the distance between the 5'-hydroxyl and the 3'-phosphotyrosine linkage to >11 Å. Id.

Figure 1B:
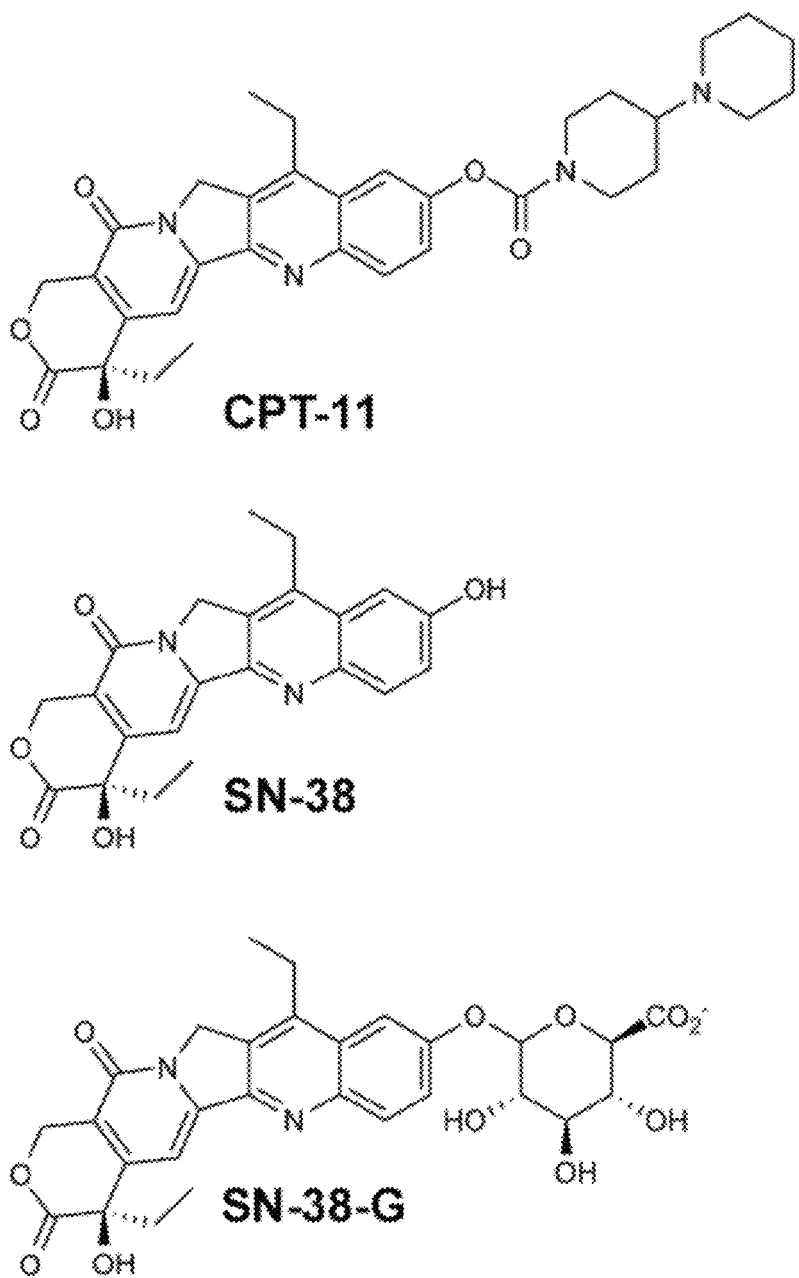
FIG. 1B shows the structure of irinotecan, as well as its active (SN-38) and inactive (SN-38G) metabolites.

CPT-11 efficacy is severely limited by delayed diarrhea that accompanies treatment. (Mathijssen et al. (2001). *Clin. Cancer Res* 7:2182-2194). While an early cholinergic syndrome that generates diarrhea within hours can be successfully treated with atropine, the diarrhea that appears ~2-4 days later is significantly more debilitating and difficult to control. (Ma & McLeod (2003) *Curr Med Chem* 10:41-49). CPT-11 undergoes a complex cycle of activation and metabolism that directly contributes to drug-induced diarrhea (FIG. 1A). Id. CPT-11 administered by intravenous injection can traffic throughout the body, but concentrates in the liver where it is activated to SN-38 by the human liver carboxylesterase hCE1 (FIG. 1B). The SN-38 generated in the liver is eliminated from the body via glucuronidation to SN-38G by the phase II drug metabolizing UDP-glucuronosyltransferase (UGT) enzymes (FIG. 1B). (Nagar & Blanchard (2006) *Drug Metab Rev* 38:393-409). SN-38G is excreted from the liver via the bile duct and into the GI. Once in the intestines, however, SN-38G serves as a substrate for bacterial β-glucuronidase enzymes in the intestinal flora that remove the glucuronide moiety and produce the active SN-38 (FIGS. 1A-B). (Tobin et al. (2003) *Oncol Rep* 10:1977-1979). SN-38 in the intestinal lumen produced in this manner contributes to epithelial cell death and the severe diarrhea that limits CPT-11 efficacy. This effect has been partially reversed in rats using the relatively weak ($IC_{50}$=90 µM) β-glucuronidase inhibitor saccharic acid 1,4-lactone. (Fittkau et al. (2004) *J Cancer Res Clin Oncol* 130:388-394).

While broad-spectrum antibiotics have been used to eliminate enteric bacteria from the gastrointestinal tract prior to CPT-11 treatment (Flieger et al. (2007) *Oncology* 72:10-16), this approach has several drawbacks. First, intestinal flora play essential roles in carbohydrate metabolism, vitamin production, and the processing of bile acids, sterols and xenobiotics. (Cummings & Macfarlane (1997) *JPEN J Parenter Enteral Nutr* 21:357-365; Guarner & Malagelada (2003) *Lancet* 361:512-519). Thus, the partial or complete removal of enteric bacteria is non-ideal for patients already challenged by neoplastic growths and chemotherapy. Second, it is well established that the elimination of the symbiotic GI flora from even healthy patients significantly increases the chances of infections by pathogenic bacteria, including enterohemorrhagic *E. coli* and *C. difficile*. (Job & Jacobs (1997) *Drug Saf* 17:37-46; Levy & Marshall (2004) *Nat Med* 10:S122-129; Nord et al. (1984) *Am J Med* 76:99-106; Settle & Wilcox (1996) *Aliment Pharmacol Ther* 10:835-841; Sears et al. (1999) *Gastrointest Endosc* 50:841-844; Stamp (2004) *Med Hypotheses* 63:555-556; Yang & Pei (2006) *World J Gastroenterol* 12:6741-6746). Third, bacterial antibiotic resistance is a human health crisis, and the unnecessary use of antimicrobials is a significant contributor to this problem. (Levy & Marshall, 2004).

β-glucuronidases hydrolyze glucuronic acid sugar moieties in a variety of compounds. (Basinska & Florianczyk (2003) *Ann Univ Mariae Curie Sklodowska Med* 58:386-389). The presence of β-glucuronidases in a range of bacteria is exploited in commonly-used water purity tests, in which the conversion of 4-methylumbelliferyl glucuronide (4-MUG) to 4-methylumbelliferone (4-MU) by β-glucuronidases is assayed to detect bacterial contamination. (Farnleitner et al. (2002) *Water Res.* 36:975-981). While the crystal structure of human β-glucuronidase was reported in 1996 (Jain et al. (1996) *Nat Struct Biol* 3:375-381), no structure of a bacterial β-glucuronidase has been presented. In addition, whereas relatively weak inhibitors of β-glucuronidase have been reported ($K_i$ values of 25 µM to 2 mM) (Russell & Klaenhammer (2001) *Appl Environ Microbiol* 67:1253-1261), no potent and/or selective inhibitors of the bacterial enzymes have been presented.

Results:

*E. coli* β-Glucuronidase Crystal Structure:

To understand bacterial β-glucuronidase activity and inhibition, we over-expressed, purified and crystallized full-length *E. coli* β-glucuronidase in both the apo and inhibitor-bound state for examination through x-ray diffraction. Native data were collected to 2.5 Å resolution and data for crystals containing inhibitor-bound enzyme were collected to 2.4 Å resolution; however, initial attempts at molecular replacement using the previously solved human β-glucuronidase model (PDB: 1 bhg, (Jain et al. (1996) *Nat Struct Mol Biol* 3:375-381)) were unsuccessful. As such, selenomethionine substituted *E. coli* β-glucuronidase was expressed, purified and crystallized to acquire necessary experimental phases to solve the bacterial structure. Selenomethionine crystal data were collected to 2.9 Å, and experimental phases were acquired using the SAD method. These phases were used to build the initial model. Molecular replacement using the SeMet model was utilized on both the native and inhibitor-bound structure. Data collection and final refinement statistics are shown in Table 1.

TABLE 1

Data Collection and Refinement Statistics.

Data Collection

| | | | |
|---|---|---|---|
| X-ray Source | APS SER-CAT BM-22 | | |
| Space group | C2 | | |
| Unit cell: a, b, c, (Å); α, β, γ (°) | 168.9, 77.3, 126.6; 90, 125.0, 90 | | |

| Data set | SeMet | Native | GDL-bound |
|---|---|---|---|
| Wavelength (Å) | 0.97926 | 1.0000 | 1.0000 |
| Resolution (Å) | 50.00-2.90 | 50.0-2.50 | 50.0-2.40 |
| highest shell | (3.00-2.90) | (2.59-2.50) | (2.49-2.40) |
| I/σ | 22.9 (3.7) | 21.9 (2.4) | 35.2 (4.1) |
| Completeness (%) | 99.2 (93.7) | 96.5 (82.4) | 98.6 (93.9) |
| Redundancy | 7.4 (6.3) | 5.2 (3.3) | 7.0 (6.2) |
| Phasing and Refinement | | | |
| Resolution (Å) | 50-2.9 | 50-2.5 | 50-2.4 |
| No. reflections | 26483 | 43507 | 50982 |
| Mean figure of merit | 0.74 | | |
| $R_{work}$ | 0.253 | 0.214 | 0.203 |
| $R_{free}$ | 0.282 | 0.267 | 0.254 |
| Molecules per asymmetric unit (AU) | 2 | 2 | 2 |
| No. of free amino acids per AU | 1192 | 1194 | 1194 |
| No. of waters per AU | 214 | 358 | 355 |
| Average B-factors | 48.8 | 60.5 | 55.1 |
| R.M.S. deviations | | | |
| Bond lengths (Å) | 0.016 | 0.003 | 0.010 |
| Bond angles (°) | 2.223 | 0.815 | 1.580 |
| Ramachandran (%) | | | |
| Preferred | 96.7 | 97.0 | 98.4 |
| Allowed | 2.7 | 2.4 | 1.3 |
| Outliers | 0.6 | 0.6 | 0.3 |

Figure 2:
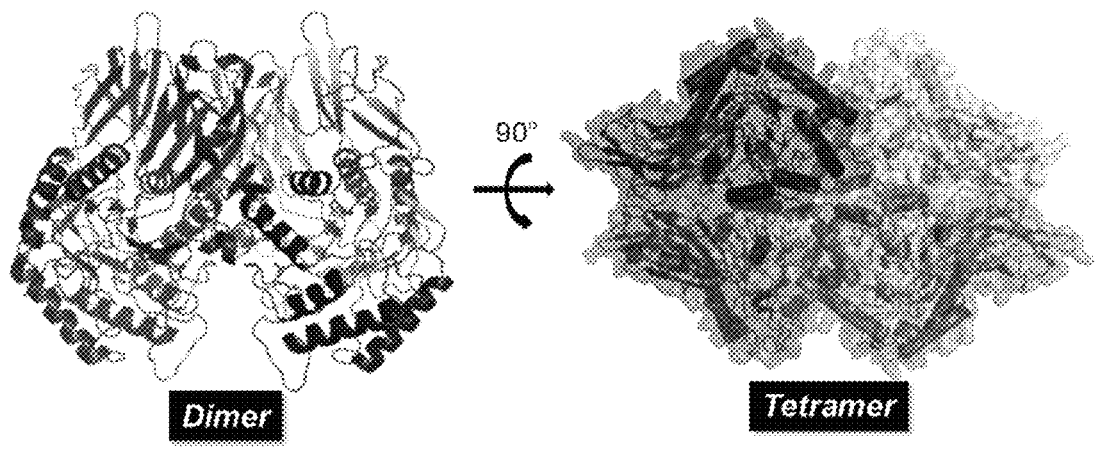
FIG. 2A shows a three-dimensional image of an E. coli β-glucuronidase dimer and tetramer.
FIG. 2B shows a crystallographic image of an E. coli β-glucuronidase tetramer in its active form.
Figure 2:
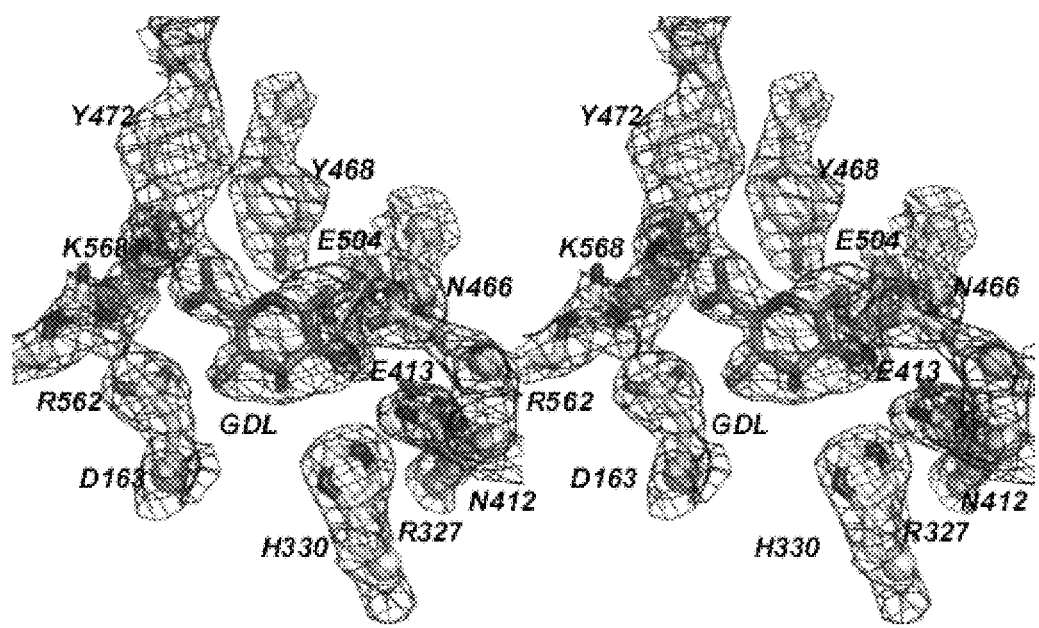

The asymmetric unit in both the native and inhibitor-bound structures contains two monomers, each composed of 597 ordered residues (FIG. 2A). Two residues at the C-terminus of the enzyme, K602 and Q603, lacked electron density, as did a disordered loop region from 363-369; as such, these regions were not placed in the final model. The N-terminal domain of *E. coli* β-glucuronidase (residues 1-180) contains 12 β-strands and two short α-helices, which resembles the sugar binding domain of the second family of glycosyl hydrolases[30]. The C-terminal domain (274-603) forms an αβ-barrel (Jacobson et al. (1994) *Nature* 369:761-766) composed of 8 short β-strands and 9 α-helices, and contains the active site residues E413 and E504. Between the N- and C-terminal domain (181-273) exists an immunoglobin-like β-sandwich domain consistent with other family 2 glycosyl hydrolases containing 7 β-strands. Id. The three domains of the protein were assigned using BLAST. (Marchler-Bauer et al. (2009) *Nucleic Acids Res* 37:13205-210). Crystallographic symmetry generates the tetramer (FIG. 2B) expected to be the active form of the enzyme as calculated by gel filtration (data not shown).

Figure 5:
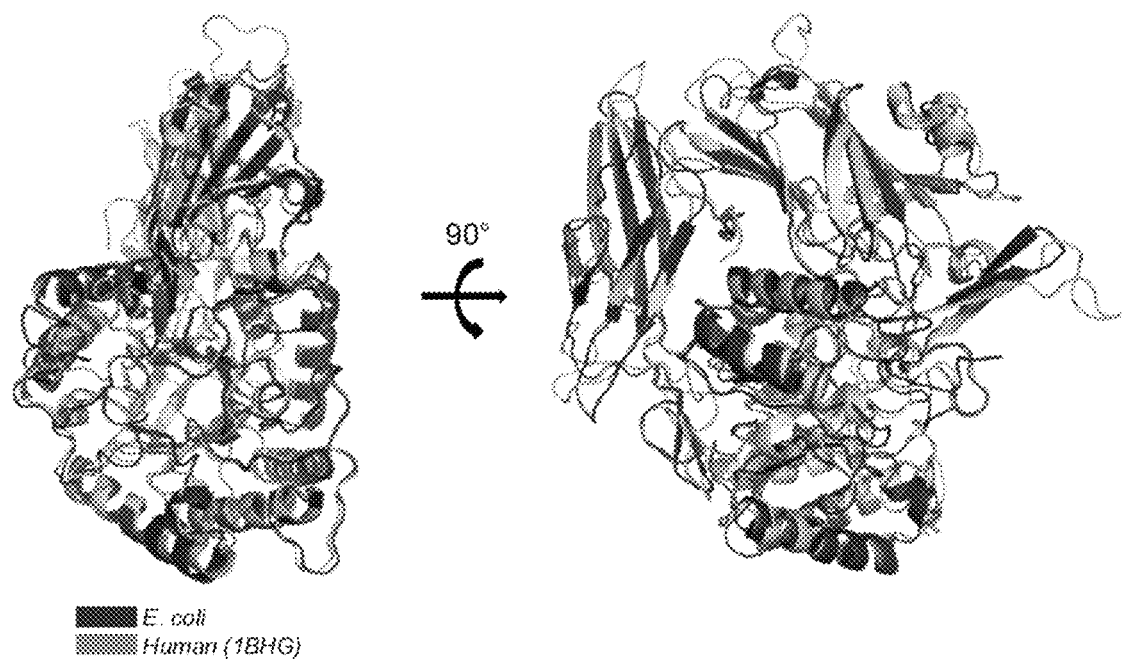
FIG. 5 shows a superimposed image of E. coli β-glucuronidase and Homo sapiens β-glucuronidase.
Figure 6:
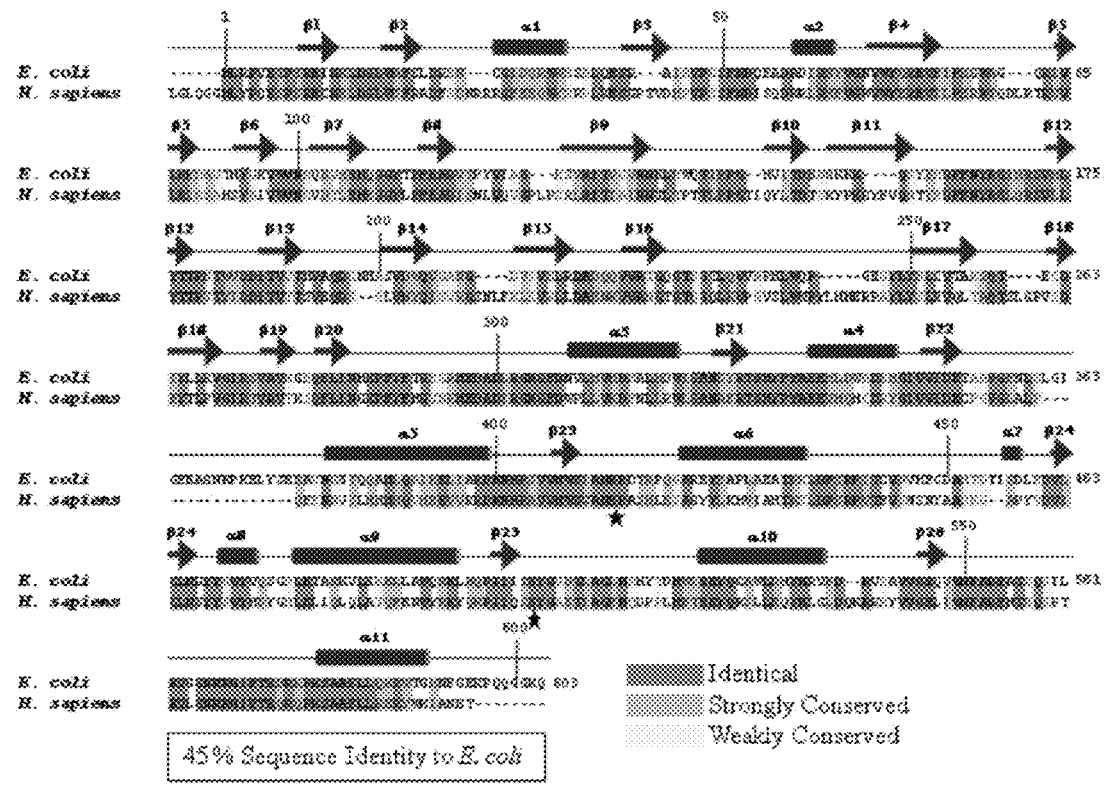
FIG. 6 shows an alignment of primary β-glucuronidase sequences from E. coli (see SEQ ID NO: 1) and H. sapiens (see SEQ ID NO: 2).

Superimposing the *E. coli* β-glucuronidase structure with the structure of the human enzyme reveals 1.4 Å r.m.s.d. over 565 equivalent Cα positions (FIG. 5). The *E. coli* structure contains one loop of ~12-17 residues in length not found in the human structure. Furthermore, the human structure contains structural elements not seen in the bacterial structure, including two loops approximately 9-11 residues longer than the equivalent *E. coli* loop, and two short helices, which are unstructured loops in the bacterial structure. In spite of these differences, the active sites of the bacterial and human enzymes align well, although in the unliganded *E. coli* structure a 7-8 residue loop is disordered in the absence of the inhibitor (see below). Other major differences between the human and *E. coli* structures can be seen in solvent-exposed regions, such as loop residues that shift by 5.6-12.4 Å between the two proteins. An alignment of the primary β-glucuronidase sequence from *E. coli* and *Homo sapiens* reveal a 45% identity relative to the *E. coli* sequence (FIG. 6). In addition, only one residue within 5 Å of the putative catalytic residues is not conserved between the two sequences.

Figure 3A:
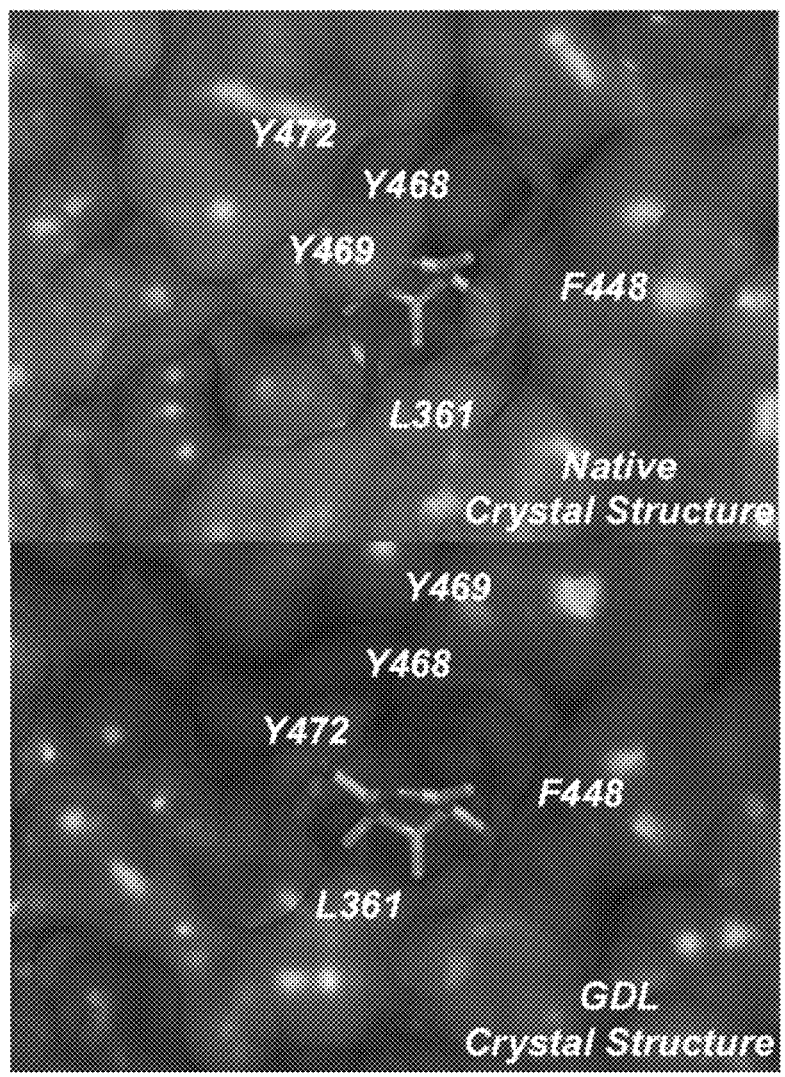
FIG. 3A shows an illustration of a native crystal structure of E. coli β-glucuronidase in which the active site is occluded by a loop (top image), and an image of a glucaro-δ-lactam (GDL)-bound E. coli β-glucuronidase in which the loop shifted (bottom image).
Figure 3B:
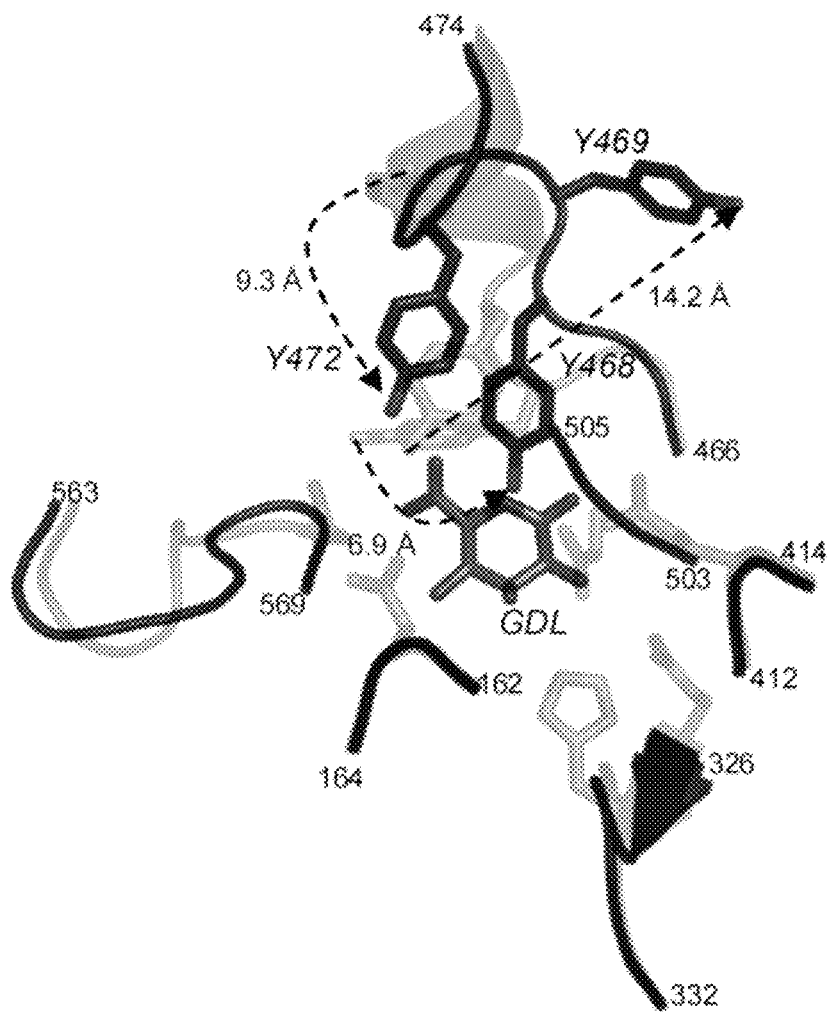
FIG. 3B shows a graphic representation of the loop shifting at the active site.
Figure 7:
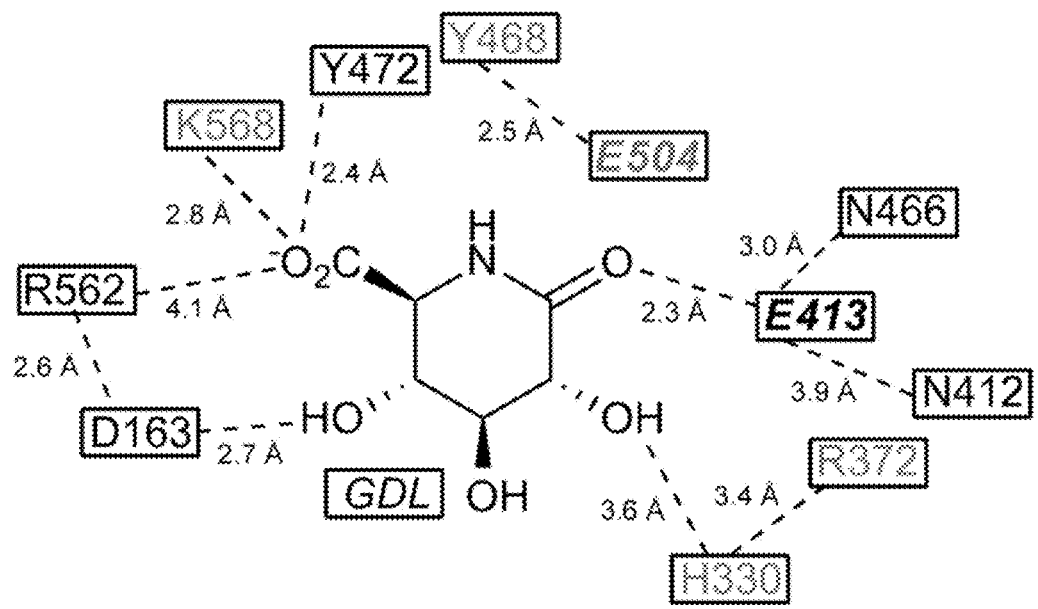
FIG. 7 shows an illustration of residues of interest for the interaction of GDL with the active site of β-glucuronidase.
Figure 8:
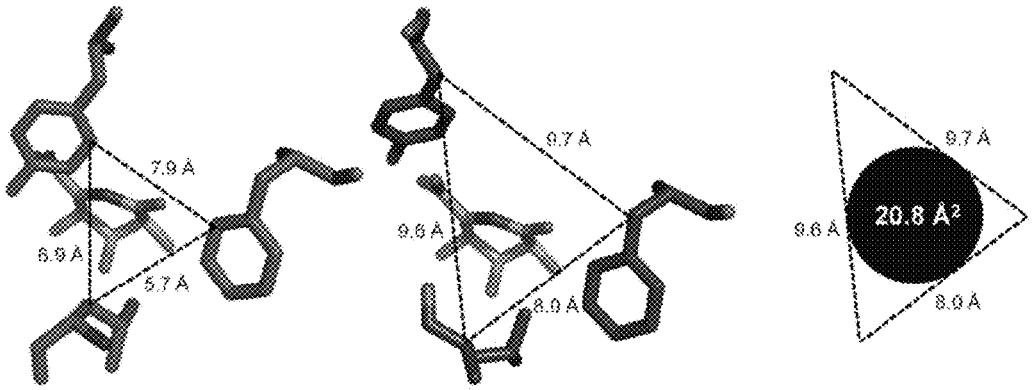
FIG. 8 shows a modeling of the shift in the active site of β-glucuronidase.

The 2.4 Å resolution glucaro-δ-lactam (GDL)-bound structure reveals a single clear binding mode of the inhibitor within the β-glucuronidase active site (FIG. 2B). GDL forms direct contacts with four amino acids (D163, R562, K568, Y472, H330) and one of the catalytic residues (E413), and is located 2.8 Å from the second catalytic residue, E504 (FIG. 7). The inhibitor-bound structure shares 1.2 Å r.m.s.d. over 597 equivalent Cα atoms when superimposed on the 2.5 Å resolution structure of the native, unliganded enzyme. The most significant site of difference (shifts in backbone position ≥2.8 Å) between the two structures occurs at the active site (FIG. 3A-B). The entrance to the active site in the native structure is occluded by the 466-476 loop that contains tyrosines 468, 469 and 472, such that this loop would clash sterically with the observed position of the GDL inhibitor (FIG. 3A). In the inhibitor-bound structure, this loop has shifted in position to relocate these aromatic residues 7-14 Å away and allow the GDL molecule to bind (FIGS. 3A-B). Upon this shift, the open area of the active site presents itself on the surface of the molecule, which results in a shift from 10.9 Å$^2$ (unliganded) to 20.8 Å$^2$ (inhibitor-bound) (see FIG. 8), and Y472 forms a direct contact with the GDL molecule (FIG. 7). Thus, a conformational change is involved in inhibitor binding to the *E. coli* β-glucuronidase active site.

Figure 4A:
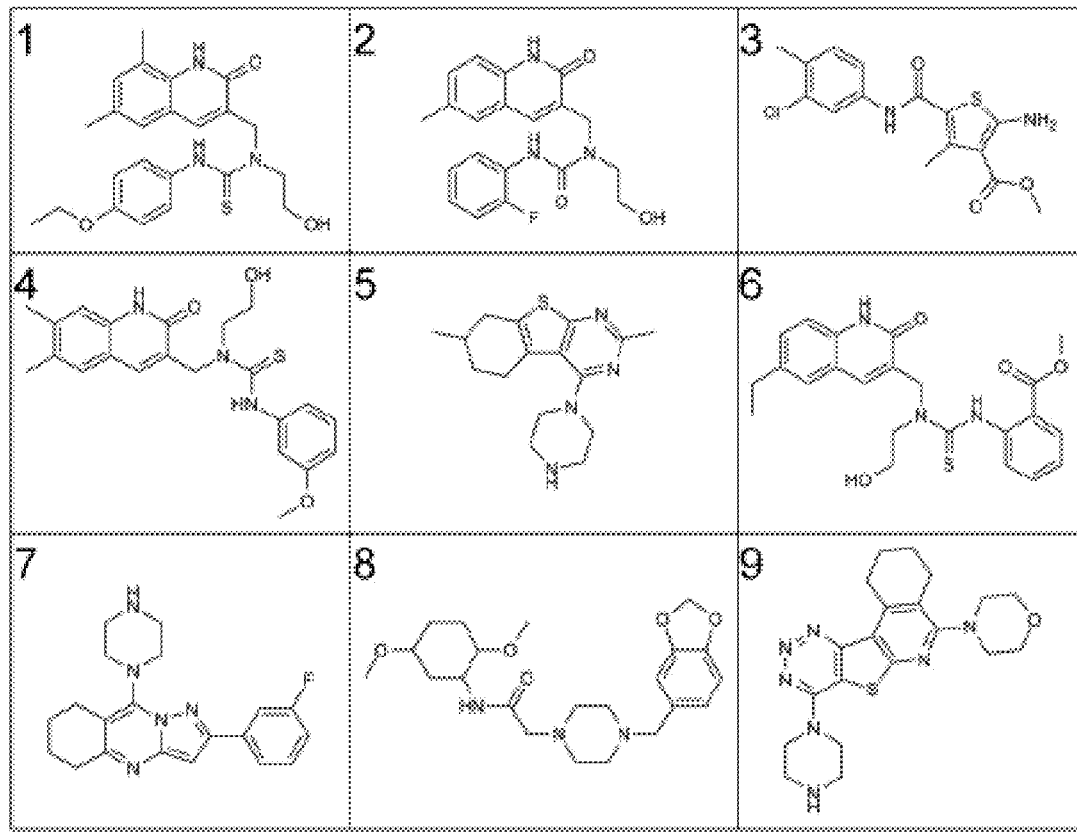
FIG. 4A shows a structure of each of the nine selective β-glucuronidase inhibitors described herein.
Figure 9:
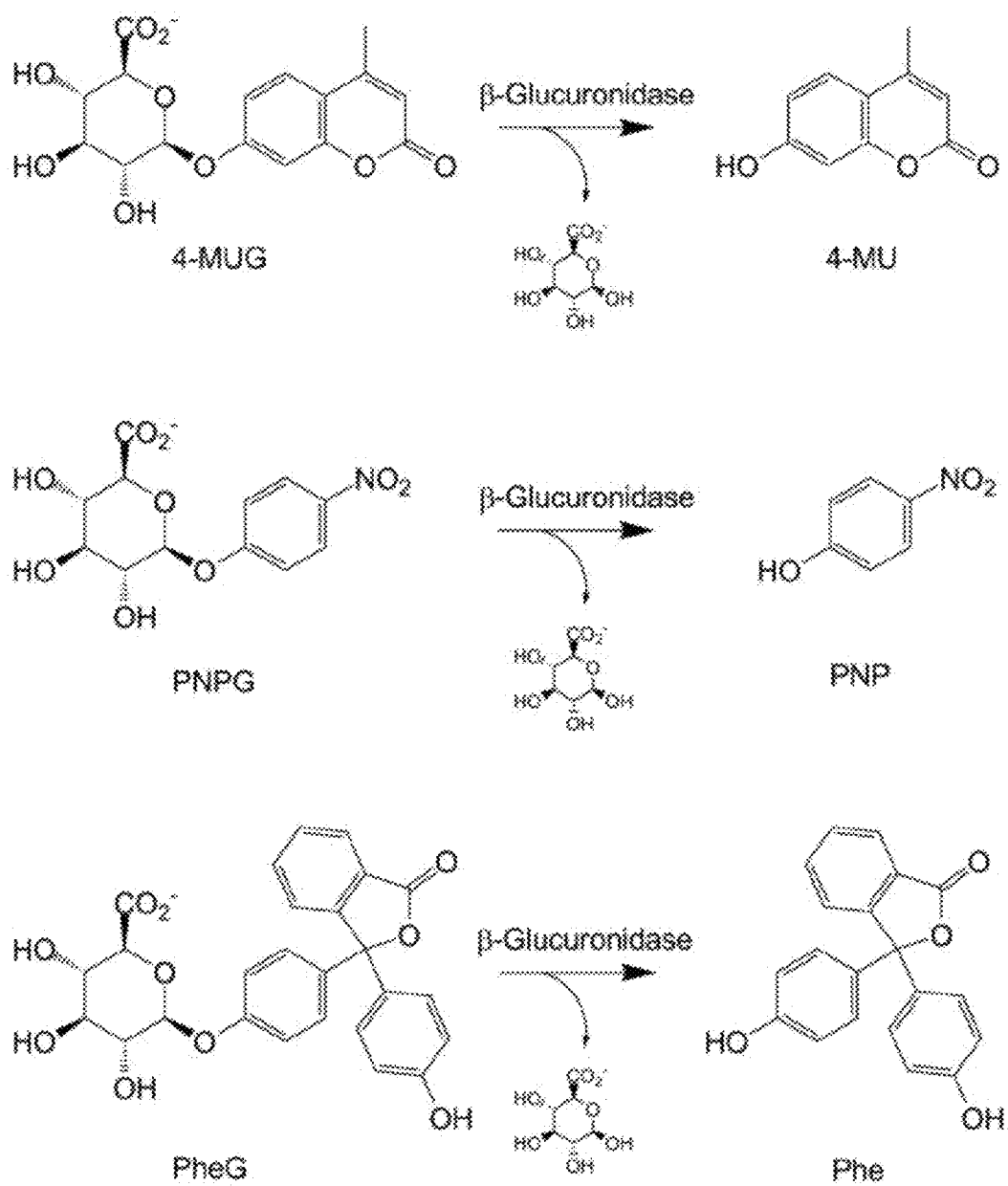
FIG. 9 shows illustrations of various substrates for β-glucuronidase assays.

Inhibitors Identification through High-Throughput Screening:

To discover novel inhibitors of *E. coli* β-glucuronidase, high-throughput screening was conducted using a 35,000-compound chemical library. A well established β-glucuronidase assay was also employed, in which the conversion of 4-methylumbelliferyl-glucuronide (4-MUG) to 4-methylumbelliferone (4-MU) is monitored by measuring the increase in 4-MU fluorescence (excitation at 365 nm, emission at 450 nm) (FIG. 9). This assay is widely employed to test water samples for bacterial contamination. (Farnleitner, 2002). It exhibited robust characteristics, with a screening Z-score of 0.84. (Zhang et al. (1999) *J Biomol Screen* 4:67-73). The hit rate was 0.3% for the 100 compounds that produced 90% inhibition or better, exhibited good Hill coefficients and R$^2$ values for inhibition curves of 0.99 or better. Nine compounds representative of the chemical diversity of the hits were chosen for further investigation (FIG. 4A). It was noted, however, in considering the chemical structures of these hits that the potential for absorbance or fluorescence was possible and may interfere with subsequent characterization in vitro or in cells. For example, compounds 1-4,6,7 and 9 were found to absorb at ~355 nm, close to the excitation wavelength of the 4-MUG assay (data not shown).

Thus, two other β-glucuronidase activity assays were employed to examine the potency of inhibitors both in vitro and in cell-based studies. An absorbance assay based on the conversion of p-nitrophenyl glucuronide (PNPG) to p-nitrophenol (PNP) (Szasz (1967) *Clin Chem* 13:752-759), which absorbs at 410 nm, was employed as the primary in vitro assay (FIG. 9). A secondary assay involving the conversion of phenolphthalein glucuronide (PheG) to phenolphthalein (Phe), which absorbs at 540 nm, was also employed (FIG. 9). Id.

Figure 10:
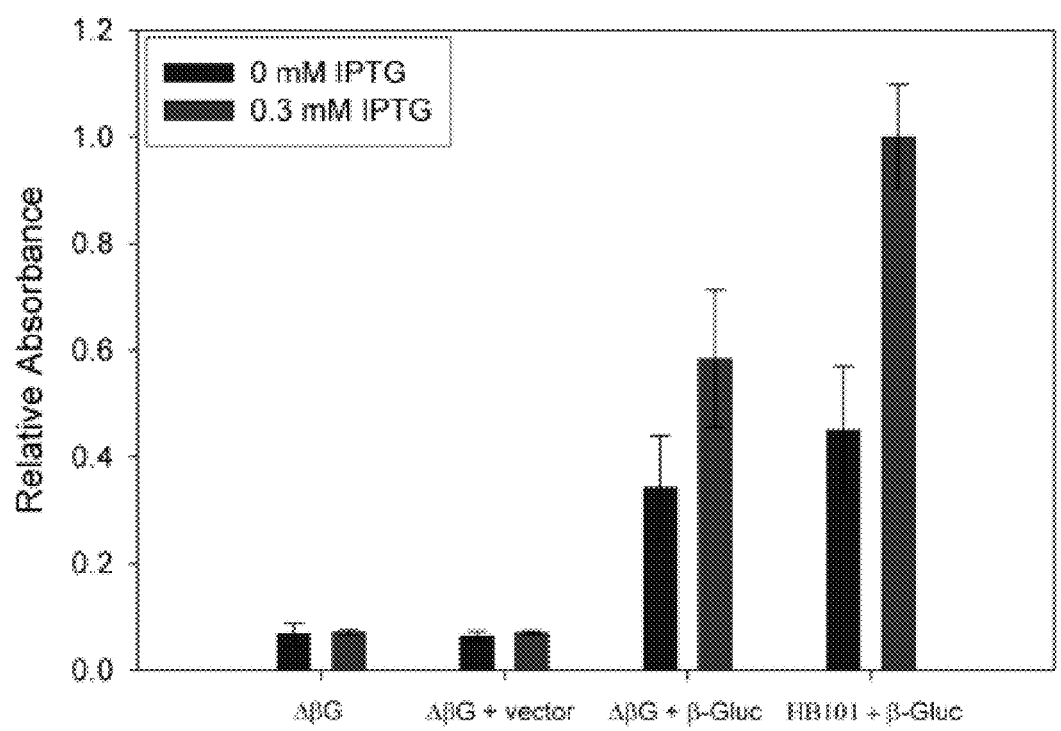
FIG. 10 shows a graph depicting a reduction in absorbance of mutant E. coli lacking β-glucuronidase or a mutant E. coli having a vector encoding for β-glucuronidase compared to wild-type E. coli (left bar is 0 mM IPTG; right bar is 0.3 mM IPTG) (abscissa is E. coli cell type; ordinate is relative absorbance).
Figure 11:
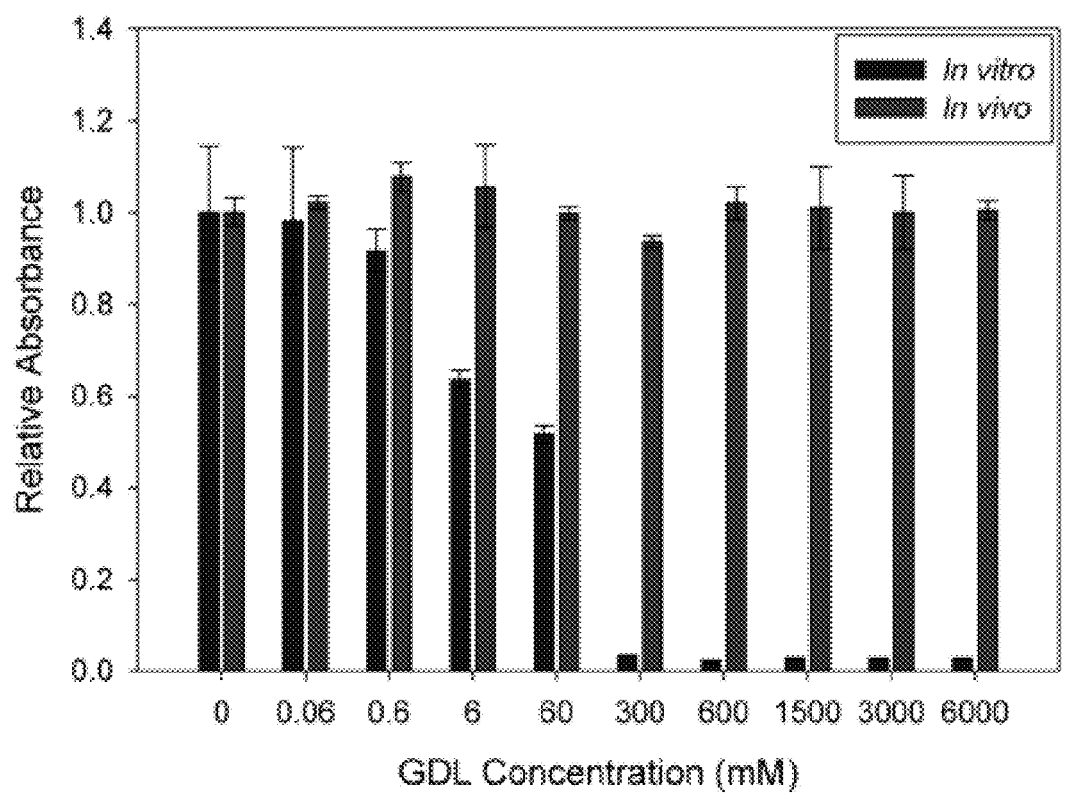
FIG. 11 shows a graph depicting a relatively weak effect of GDL in vitro (left bar is in vitro treatment; right bar is in vivo treatment) (abscissa is GDL concentration (mM); ordinate is relative absorbance).

Both assays were validated in vitro and in living cells, and the wavelengths monitored did not overlap with absorbance characteristics of putative inhibitors (data not shown). Importantly, as outlined below, these assays recapitulated the in vitro high-throughput screening results obtained with the 4-MUG substrate. Control experiments were also performed to show that the enzyme activity detected in cell-based assays was dependent on the presence of expressed β-glucuronidase. For example, *E. coli* cells lacking a β-glucuronidase gene showed no enzyme activity using PNPG as a substrate; but when a bacterial β-glucuronidase was expressed in those and wild-type cells lines, enzyme activity increased accordingly (FIG. 10). The glucaro-δ-lactam (GDL) inhibitor examined in the crystal structure of *E. coli* β-glucuronidase exhibited relatively in vitro weak IC50 values of 45±3.1 µM using PNPG and was ineffective in cells (FIG. 11).

Figure 4B:
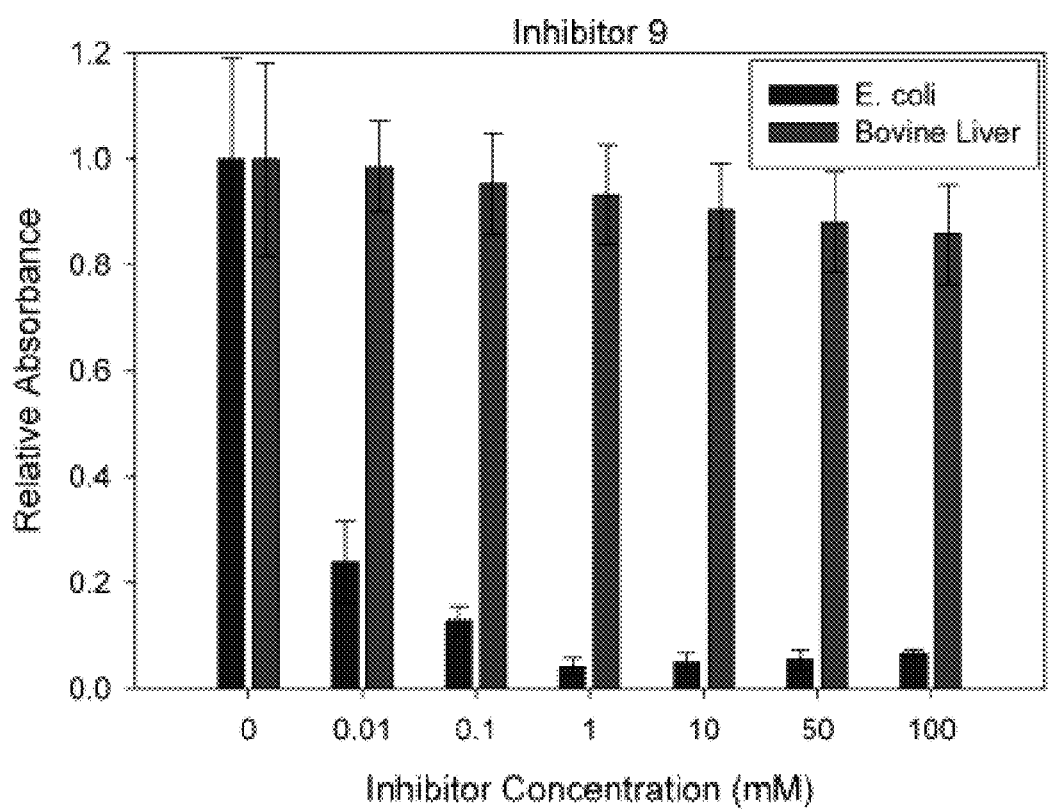
FIG. 4B shows a graph depicting a reduction in absorbance that represents decreasing β-glucuronidase with an increase in β-glucuronidase inhibitor concentration (inhibitor 9) of E. coli β-glucuronidase (left bar at each concentration) compared to bovine β-glucuronidase (right bar at each concentration) (abscissa is inhibitor concentration in mM; ordinate is relative absorbance).
Figure 12:
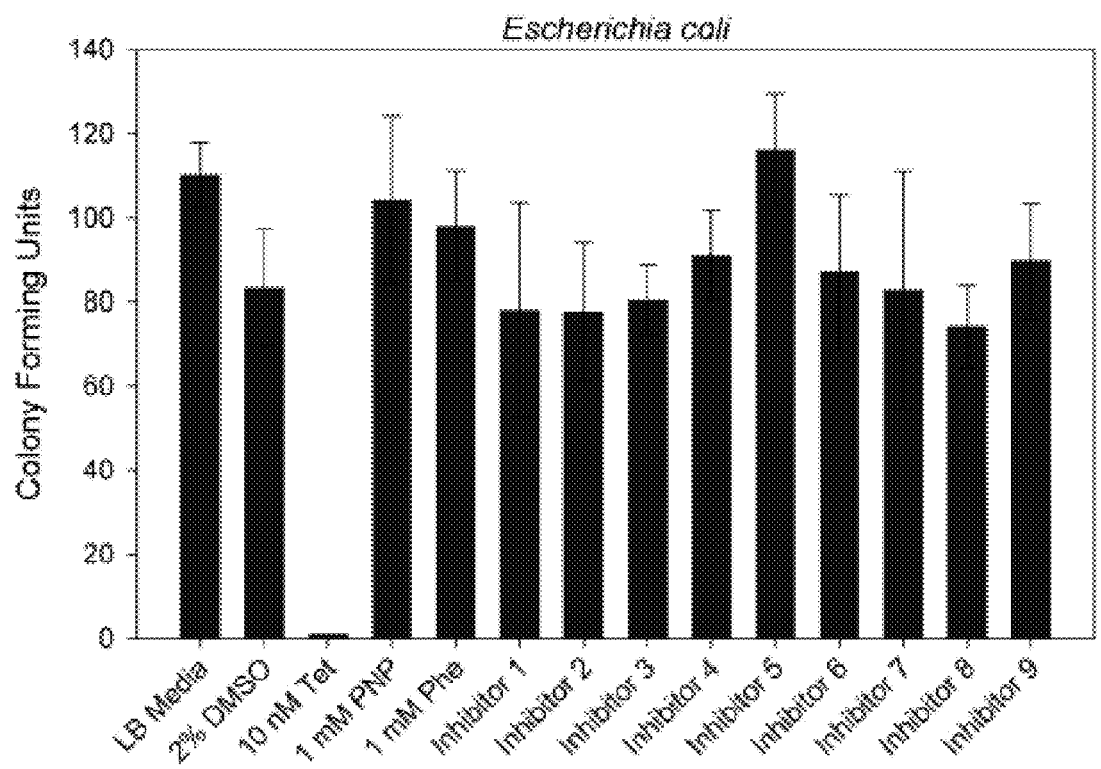
FIG. 12 shows a graph depicting a lack of significant effect of the selective β-glucuronidase inhibitors on viability/cell survival of E. coli (abscissa is treatment condition; ordinate is colony forming units).

Potent Inhibition In Vitro and in Living Aerobic and Anaerobic Bacterial Cells:

The nine representative compounds chosen from the high-throughput screening results (FIG. 4A) were all more potent than glucaro-δ-lactam in vitro, and eight of the nine were effective in living cells as well (Table 2). FIG. 4B shows a typical graph of the reduction in absorbance representing decreasing β-glucuronidase activity with an increase of inhibitor concentration. In vitro, six (1, 2, 4, 5, 8 and 9) of the nine inhibitors had nanomolar-level IC$_{50}$ values, and the other three (3, 6 and 7) had values of less than 2 µM. Compound 9 proved to be the strongest inhibitor with an IC$_{50}$ value of 1.17±0.50 nM (Table 2). Cell-based assays in living *E. coli* cells were also conducted on each of the nine compounds; EC$_{50}$ values are presented Table 2. The potency of inhibition improved in cells relative to in vitro for compounds 1, 2, 4, 5, and 7; however, compounds 6 and 8 showed no improvement, and compound 3 was ineffective. The efficacy of compound 9 remained strong in cells, with an EC$_{50}$ value of 3.58±1.80 nM. To assess the validity of these results, cell survival was tested in the presence of 100 µM of each of the nine inhibitors, as well as 1 mM of the hydrolysis products, PNP and Phe. The nine compounds exhibited no significant effect on cell survival (FIG. 12). Thus, potent inhibition of β-glucuronidase activity was achieved in *E. coli* cells growing in aerobic conditions.

TABLE 2

Effect of the Inhibitor Compounds in Two β-Glucuronidase Assays.

| Inhibitor | PNPG | | PheG | |
|---|---|---|---|---|
| | IC$_{50}$ (nM) | EC$_{50}$ (nM) | IC$_{50}$ (nM) | EC$_{50}$ (nM) |
| 1 | 282.5 ± 26.05 | 17.7 ± 7.42 | 277.3 ± 30.4 | 29.0 ± 3.33 |
| 2 | 585.7 ± 31.1 | 233.2 ± 2.99 | 600.8 ± 55.3 | 221.2 ± 22.01 |
| 3 | 1624 ± 1.32 | | 1688.9 ± 24.12 | |
| 4 | 369.3 ± 2.51 | 28.3 ± 2.11 | 377.8 ± 13.71 | 33.2 ± 8.18 |
| 5 | 230.6 ± 1.17 | 92.4 ± 1.34 | 212.6 ± 17.9 | 99.9 ± 23.0 |
| 6 | 1058.2 ± 3.54 | 1322.8 ± 1.15 | 1067.2 ± 33.2 | 1302.5 ± 15.7 |
| 7 | 1204.6 ± 1.70 | 811 ± 1.35 | 1266.4 ± 86.12 | 913.3 ± 20.4 |
| 8 | 740.1 ± 20.4 | 776.9 ± 6.44 | 721.7 ± 31.3 | 793.1 ± 27.9 |
| 9 | 1.17 ± 0.50 | 3.58 ± 1.80 | 0.984 ± 0.37 | 3.41 ± 1.13 |

Figure 4C:
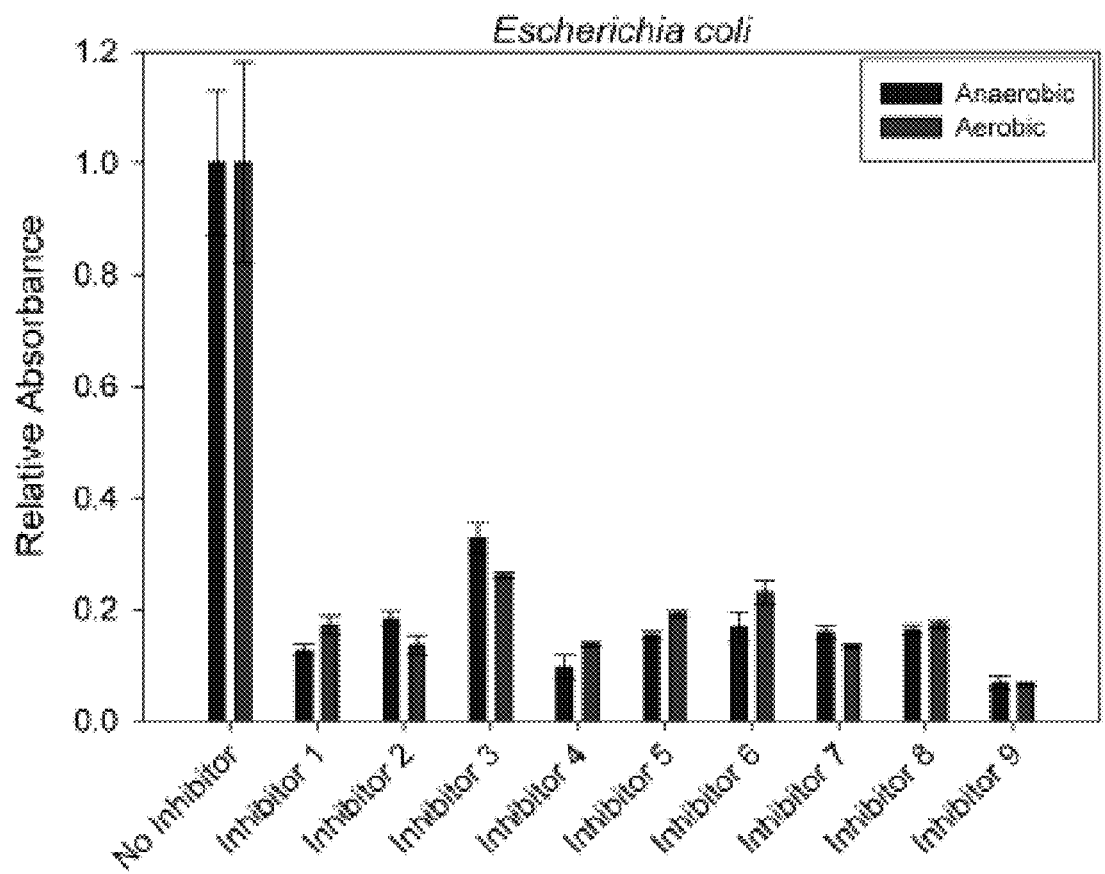
FIG. 4C shows a graph depicting a significant effect of the selective β-glucuronidase inhibitors on β-glucuronidase activity of E. coli under anaerobic (left bar at each treatment) and aerobic (right bar at each treatment) conditions (abscissa is treatment condition; ordinate is relative absorbance).
Figure 4D:
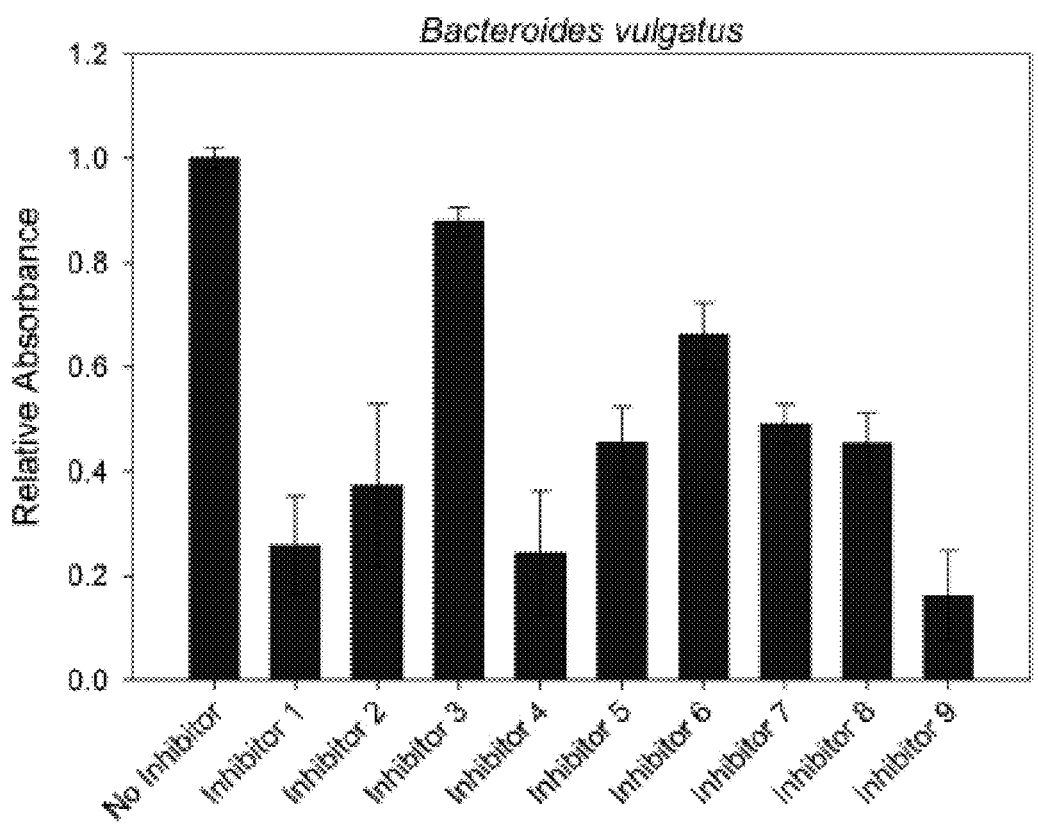
FIG. 4D shows a graph depicting efficacy of the selective β-glucuronidase inhibitors on the obligate anaerobe Bacteroides vulgatus (abscissa is treatment condition; ordinate is relative absorbance).

Because over 99% of the bacterial species present GI tract are obligate anaerobes (Sears (2005) *Anaerobe* 11:247-251), *E. coli* cells grown under anaerobic conditions were tested, as well as other relevant anaerobic bacterial species. (Hawksworth et al. (1971) *J Med Microbiol* 4:451-459). The cell-based assay using anaerobic *E. coli* yielded similar results to those of the aerobic conditions (FIG. 4C). Furthermore, in-cell assays using the obligate anaerobe *Bacteroides vulgatus* also demonstrated inhibitor efficacy (FIG. 4D), *L. reuteri* and

*B. infantis* were also tested, which do not contain the β-glucuronidase gene, (Russell & Klaenhammer, 2001; Grill et al. (1995) *Curr Microbiol* 31; 23-27) and found no evidence of enzyme activity or inhibitor impact on assay signal (data not shown). As such, these cell lines are effective negative controls. Taken together with the in vitro and cell-based data outlined above, these results confirm that we have identified several novel potent inhibitors of β-glucuronidase activity that are effective in living aerobic and anaerobic bacterial cells lines but do not impact microbial cell survival.

Figure 13:
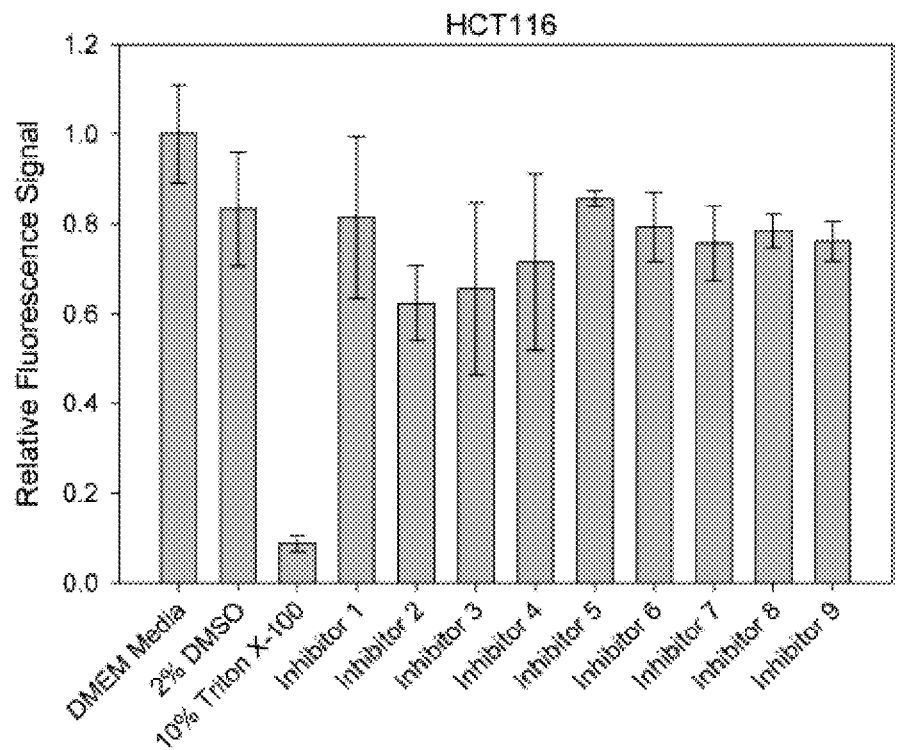
FIG. 13 shows a graph depicting a lack of cytotoxicity of the selective β-glucuronidase inhibitors on human colonic cells (abscissa is treatment condition; ordinate is relative fluorescence signal).

With the identification of novel inhibitors of β-glucuronidase activity, the next step was taken to further characterize the compounds' effects on human intestinal cells, similar to those likely to be encountered in the colonic region of the gastrointestinal tract. HCT116 (Brattain et al. (1981) *Cancer Res* 41:1751-1756), human colonic epithelial cells were treated with each of the nine inhibitors to test the viability of these cells to grow in their presence. Using the CellQuanti-Blue" " Assay Kit, the HCT116 cells were treated with the inhibitors, and checked for human cytotoxicity; the results show that the potent inhibitors do not effect human colonic cells (FIG. 13). The specificity of the nine compounds was tested by exploring their effects on a mammalian β-glucuronidase. In vitro assays were conducted using bovine liver β-glucuronidase in a similar manner to that of the bacterial enzyme assay. With a range of 0 to 100 µM inhibitor concentration of each of the nine inhibitors, it was observed that they have little to no effect on the activity of this mammalian β-glucuronidase (FIG. 4B).

Figure 14A:
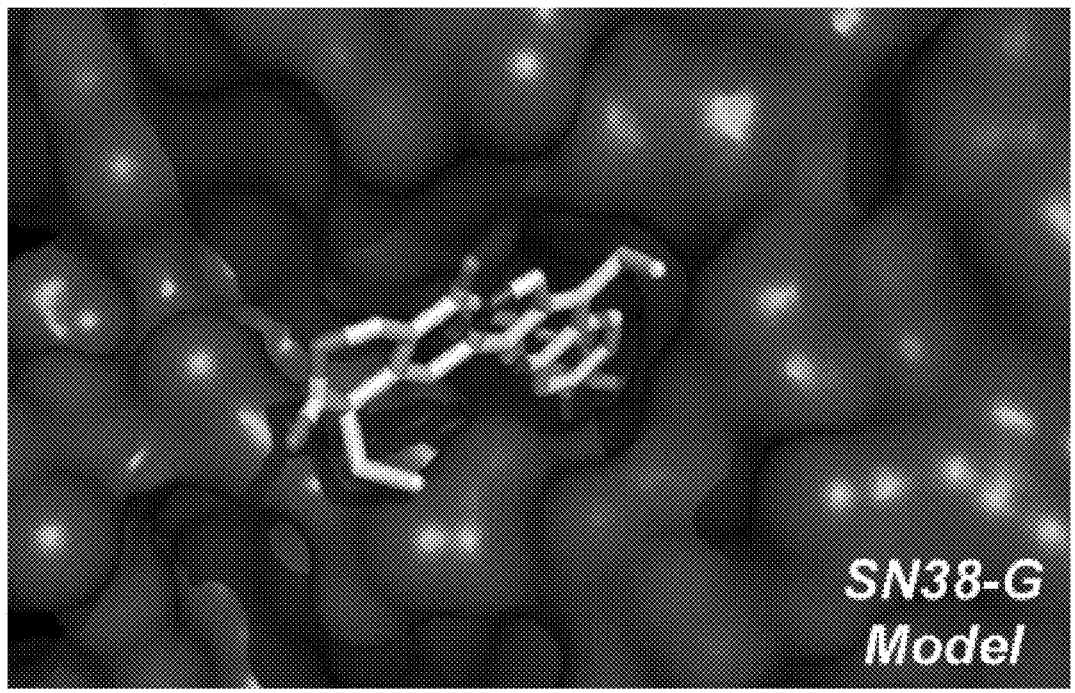
FIG. 14A shows illustration of an E. coli β-glucuronidase in which the active site is bound to SN-38G.
Figure 14B:
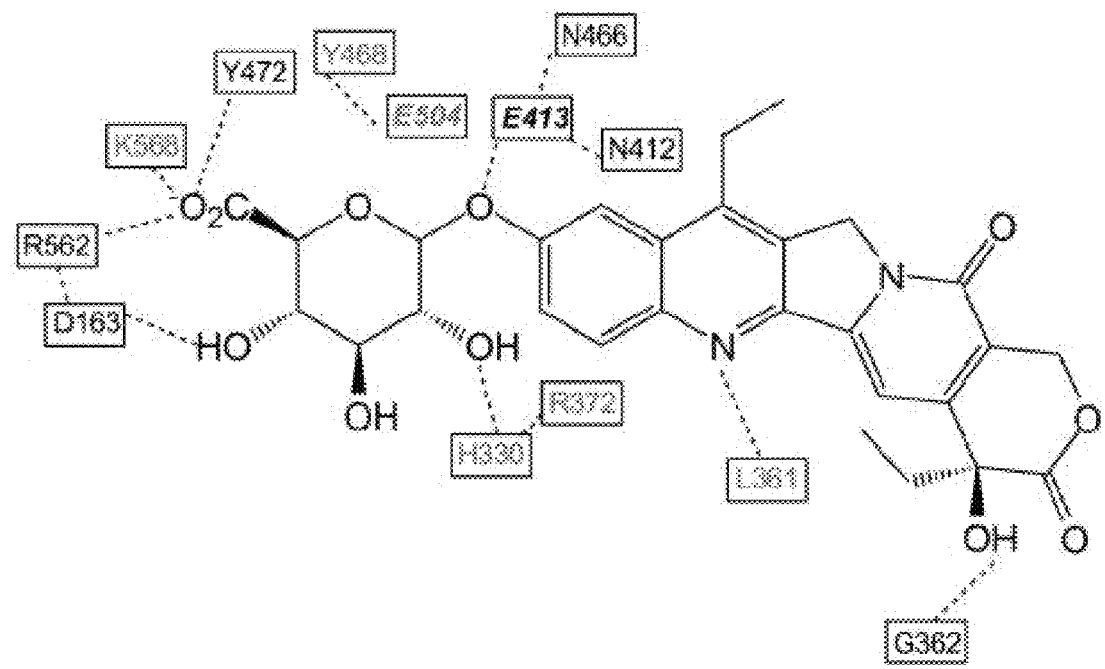
FIG. 14B shows a structural representation of FIG. 14A.
Figure 14C:
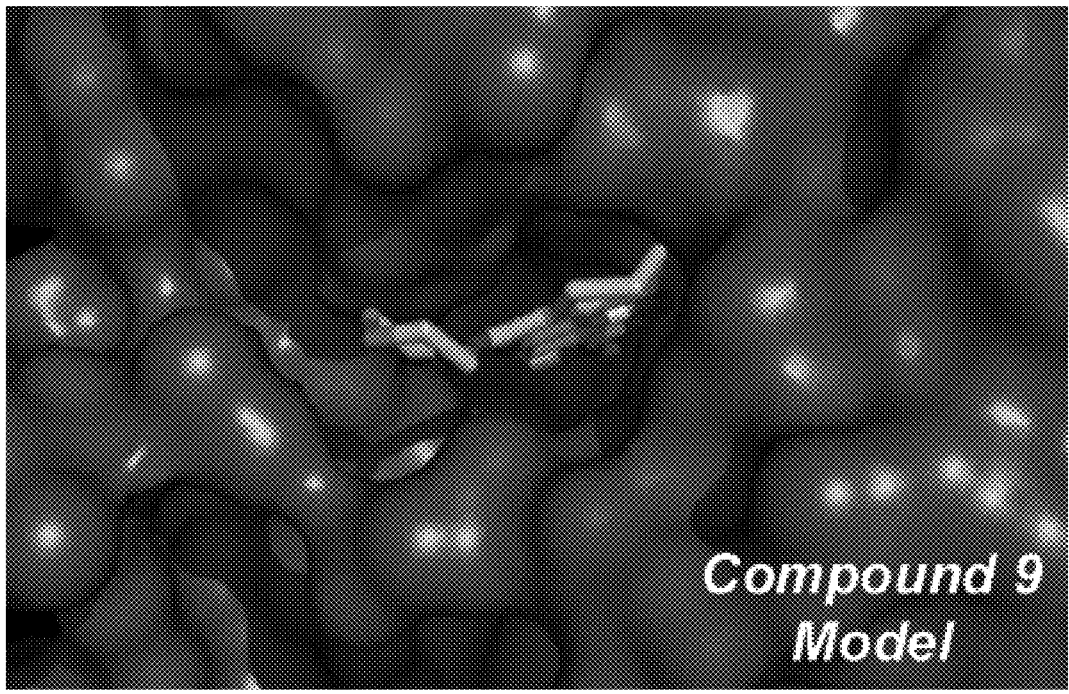
FIG. 14C shows an illustration an E. coli β-glucuronidase in which the active site is bound to inhibitor 9.
Figure 14D:
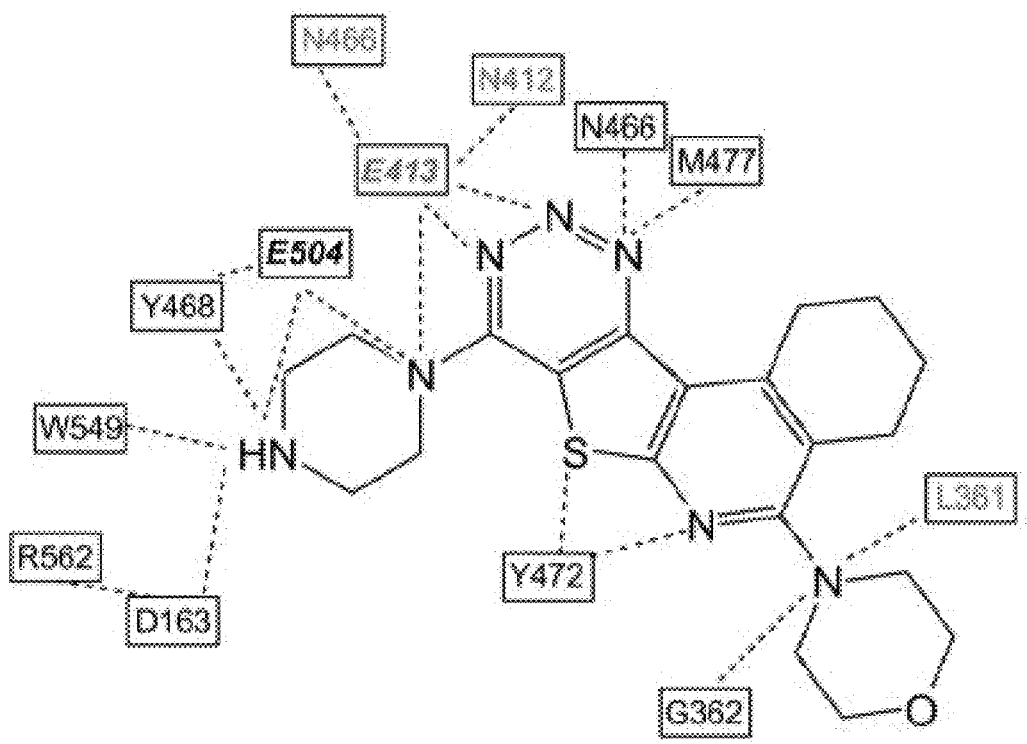
FIG. 14D shows a structural representation of FIG. 14C.

Discussion:

The first crystal structure of a bacterial β-glucuronidase enzyme is reported herein, as well as structures of both the unliganded protein and complexed with an inhibitor. A significant shift in the position of an active site loop upon ligand binding reveals that conformational change may be involved in the formation of all substrate and inhibitor complexes with the enzyme (e.g., FIG. 3B). The residues on this loop (466-474 and 503-505) are nearly fully conserved between the bacterial and human β-glucuronidases; thus, a similar "induced fit" mechanism may be at play in eukaryotic β-glucuronidases as well. Importantly, knowledge of the changes in structure that can occur at the bacterial β-glucuronidase active site can be employed in the in silica screening and validation of additional potential enzyme inhibitors. In addition, the binding of SN-38G (see FIG. 1) and compound 9 (see FIG. 4A) into the β-glucuronidase active site (FIGS. 14A-B) were modeled. Several critical interactions are formed between conserved catalytic gorge residues on the enzyme (e.g., Y468, Y472, N466, and D163) and functional groups on the substrate and inhibitor. Additionally, both compounds take on a curved shaped, allowing them to fit tightly into the curved tunnel of the active site. These models provide a useful place to begin to develop improved inhibitors by structure-based design.

The nine compounds that were characterize further from the 300 plus hits from high-throughput screening all are effective inhibitors of the β-glucuronidase enzyme in vitro (with $IC_{50}$s of 1 nM-1.6 µM), and eight of the nine maintain 3 nM-1.3 µM efficacy in living bacterial cells. Furthermore, they exhibit β-glucuronidase inhibition in anaerobic conditions and against an obligate anaerobe, *Bacteroides vulgatus*, known to be a significant component of the human gastrointestinal microflora. (Sears, 2005). Importantly, however, the inhibitors characterized here do not impact bacterial cell growth or survival. This was a desired characteristic of compounds designed to be used in conjunction with CPT-11. Effective β-glucuronidase inhibitors would reduce SN-38 reactivation in the GI without eliminating these commensal bacteria that promote health and prevent infection by opportunistic bacteria like *Clostridium difficile*. (Guarner & Malagelada 2003; Job & Jacobs, 1997).

In medicinal applications, these potent inhibitors can contact the human epithelial cell lining in the intestine. HCT116 human colonic epithelial cells were incubated with the nine compounds in order to test them for cytotoxic effects on mammalian cells. As shown (FIG. 13), the inhibitors have little to no cytotoxicity, and these cells continue to be viable in their presence. As such, novel potent inhibitors have been discovered that not only inhibit β-glucuronidase in vivo, but are also non-toxic to bacterial cells lines, anaerobic and aerobic, as well as human epithelial cells known to inhabit the GI tract. This is a crucial starting point to move into more clinical settings.

To assess the selectivity of the nine compounds a mammalian β-glucuronidase, from bovine liver, was incubated and tested for enzyme activity in their presence. The nine compounds appear to not inhibit this mammalian enzyme as they do the bacterial (data not shown, see FIG. 4B for example). These results suggest that the inhibitors show a fair amount of selectivity towards the bacterial enzyme. Preliminary analysis via sequence and structural alignment (see FIGS. 5-6) indicates that the ~12 residue loop (362-374) in the *E. coli* β-glucuronidase that hovers over the active site opening, of which is missing in the human enzyme (bovine liver β-glucuronidase is 82% identical and is also missing this loop region), may play a part in this issue. The major role of the mammalian version of the enzyme is to cleave the glucuronic acid moiety from long chain glycosaminoglycans. (Ray et al. (1999) *J Hered* 90:119-123; Eudes et al. (2008) *Plant Cell Physiol* 49:1331-1341). As such, these enzymes must have the ability to accommodate these large substrates. The lack of this loop region would allow for a more open active site and avenue for larger substrates to reside. This loop region, which is present in the bacterial enzyme, would suggest that small molecules, such as glucuronide linked xenobiotics (Eudes, 2008) would have a tighter fit in the active site such that the enzyme would be turned "off" more frequently.

CPT-11 is currently used largely in combination with a number of well-known chemotherapeutics (Masuda et al. *J Clin Oncol* 10:1775-1780; Saltz et al. (1996) *Eur J Cancer* 32A Suppl 3:S24-31) but can still be employed as a single agent in colorectal cancer. (Armand et al. (1995) *Eur J Cancer* 31A:1283-1287; Shimada et al. (1996) *Eur J Cancer* 32A Suppl 3:Sβ-17). To improve the outcome for subject on CPT-11 alone, and potentially to allow more single agent use, one can reduce the diarrhea that limits dose intensification and efficacy. An approach can be to inhibit the β-glucuronidase enzyme known to reactivate SN-38G to SN-38 in the lower gastrointestinal tract. Such inhibitors are potent and effective in living bacterial cells, but do not kill the bacteria that inhabit the gastrointestinal tract.

Materials and Methods:

Expression and Purification of *E. coli* β-Glucuronidase.

The full-length *E. coli* β-glucuronidase gene was obtained from genomic DNA and was cloned into the pET-28a expression plasmid (Novagen) with an N-terminal 6x-Histidine tag. BL2'-DE3 competent cells were transformed with the expression plasmid and grown in the presence of kanamycin (25 ug/ml) in LB medium with vigorous shaking at 37° C. The expression was induced with the addition of 0.3 mM IPTG and further incubated for 4 hours. Cells were centrifuged at 4500×g for 20 min at 4° C. for collection. Cell pellets were resuspended in Buffer A, along with PMSF and protease inhibitors containing aprotinin and leupeptin. Resuspended cells were lysed by sonication and clarified by centrifugation. Protein was purified by Ni-chromatography column followed by gel filtration.

Selenomethionine Substituted β-Glucuronidase.

B834 competent cells were transformed with pET-28a containing the β-glucuronidase gene. SelenoMet™ Medium and Nutrient Mix (AthenaES) were prepared for growth, with 50 mg of selenomethionine added for each liter of medium. The cells were grown and induced the same as the native β-glucuronidase. The temperature was lowered to 15° C. and the cultures grown overnight with shaking.

Crystallization, Data Collection, and Phasing.

Crystals were obtained at 2 mg/mL protein in 15% PEG3350, 0.2 M Magnesium Acetate, and 0.02% Sodium Azide at 16° C. Crystals were cryo-protected with perfluoropolyether oil (Sigma) and flash cooled in liquid nitrogen. Diffraction data were collected on the 22-BM beam line at SER-CAT (Advanced Photon Source, Argonne National Laboratory). Data were indexed and scaled using HKL2000. (Otwinowski et al., "Processing of X-ray diffraction data collected in oscillation mode" 307-326 In: Methods in Enzymology, Vol. 276 (Academic Press 1997)). Selenomethionine data were collected to 2.9 Å and processed similarly. The PHENIX software suite was utilized to locate heavy atom sites and to trace a portion of the model. (Adams et al. (2002) *Acta Crystallogr D Biol Crystallogr* 58:1948-1954). An initial model was built in Coot using the SAD data and used with Phaser for molecular replacement. (Emsley & Cowtan (2004) *Acta Crystallogr D Biol Crystallogr* 60:2126-2132; McCoy et al. (2007) *J Appl Crystallogr* 40:658-674). The structure was refined using simulated annealing and torsion angle refinement in CNS, and monitored using both the crystallographic R and cross-validating R-free statistics. (Brunger (1997) *Methods Enzymol* 277:366-396). Data collection and refinement statistics are presented in Table, 1. PHENIX was used for anisotropic B-factor and TLS refinement. (Adams, 2002). The model was manually adjusted using Coot and $2F_o-F_c$ and $F_o-F_c$ electron density maps. The GDL model and definition files were generated using PRODRG. (Schuttelkopf & van Aalten (2004) *Acta Crystallogr D Biol Crystallogr* 60:1355-1363).

Inhibitor Compounds.

Purified protein was sent to NCCU-BRITE to screen various compound libraries for potential inhibitors. Nine compounds were chosen for further analysis. The compounds (FIG. 4A) were purchased from ASINEX. Each compound was provided as a solid powder and dissolved in 100% DMSO.

In Vitro β-Glucuronidase Assays.

In vitro assays were conducted at 50 µL total volume in 96-well, clear bottom assay plates (Costar). Substrates consisted of PNPG or PheG (FIG. 9) and were acquired from Sigma. The presence of the hydrolysis product of each, PNP or Phe, was measured by absorbance at 410 nm or 540 nm, respectively. Reactions were allowed to proceed for 6 hours at 37° C. and were quenched with 100 µL of 0.2 M sodium carbonate. Absorbance was measured using a PHERAstar Plus microplate reader (BMG Labtech).

Human Cell Survivability.

The nine compounds were tested for cytotoxicity in human cells. HCT116 human epithelial colonic cells were grown and cultured in DMEM medium till confluent and adherent. Cells were counted and dilutions were made to achieve a 50,000 cell count per reaction.

Mammalian β-Glucuronidase In Vitro Assays.

Bovine liver β-glucuronidase was acquired in lyophilized form from Sigma. The protein was dissolved and the assay was conducted as previously published, using PNPG as the substrate for activity detection. (Graef et al. (1977) *Clin Chem* 23:532-535). Each inhibitor was tested for an effect on mammalian β-glucuronidase activity. Reaction time and temperature were the same as previously described (see In Vitro β-Glucuronidase Assays).

Cell-Based Inhibition Assays.

HB101 *E. coli* cells were grown to an $OD_{600}$ of 0.6 in LB medium. These cells were then used for an in vivo assay. Reaction time and temperature were the same as previously described (see In Vitro β-Glucuronidase Assays). The β-glucuronidase gene (GUS) knockout cell-line (GMS407) was purchased from CGSC at Yale University. Absorbance was measured at the appropriate wavelength, depending on the substrate. Cell survivability in the presence of the nine inhibitors was tested by plating cells with each compound.

Anaerobic In Vivo Studies.

*Lactobacillus reuteri*, *Bifidobacterium infantis*, *Bacteroides vulgatus* and *Clostridium ramosum* were provided by the Sartor Lab at the University of North Carolina at Chapel Hill. Anaerobic bacteria were plated on MRS and BHI plates. Prior to streaking, plates were pre-equilibrated in an anaerobic chamber using the BD BBL™ GasPak™ Plus Anaerobic System Envelopes.

Supplemental Methods:

Expression and Purification of *E. coli* β-Glucuronidase.

The full-length *E. coli* β-glucuronidase gene was obtained from bacterial genomic DNA and was cloned into the pET-28a expression plasmid (Novagen) with an N-terminal 6×-Histidine tag. BL21-DE3 competent cells were transformed with the expression plasmid and grown in the presence of kanamycin (25 ug/ml) in LB medium with vigorous shaking at 37° C. until an $OD_{600}$ of 0.6 was attained. The expression was induced with the addition of 0.3 mM isopropyl-1-thio-D-galactopyranoside (IPTG) and further incubated at 37° C. for 4 hours. Cells were collected by centrifugation at 4500×g for 20 min at 4° C. in a Sorvall (model RC-3B) swinging bucket centrifuge. Cell pellets were resuspended in Buffer A (20 mM Potassium Phosphate, pH 7.4, 25 mM Imidazole, 500 mM NaCl), along with PMSF (2 µL/mL from 100 mM stock) and 0.05 µL/mL of protease inhibitors containing 1 mg/mL of aprotinin and leupeptin. Resuspended cells were sonicated and centrifuged at 14,500×g for 30 min in a Sorvall (model RC-5B) centrifuge to clarify the lysate. The cell lysate was flowed over a pre-formed Ni-NTA His-Trap gravity column and washed with Buffer A. The Ni-bound protein was eluted with Buffer B (20 mM Potassium Phosphate, pH 7.4, 500 mM Imidazole, 500 mM NaCl). Collected fractions were then tested for initial purity by SDS-PAGE. Relatively pure (~85%) fractions were combined and loaded into the Äktaxpress FPLC system (Amersham Biosciences) and passed over a HiLoad™ 16/60 Superdex™ 200 gel filtration column. The protein was eluted into 20 mM HEPES, pH 7.4, and 50 mM NaCl for crystallization and activity assays. Two milliliter fractions were collected based on highest ultraviolet absorbance at 280 nm. Fractions were analyzed by SDS-PAGE (which indicated >95% purity), combined, and concentrated to 10 mg/mL for long-term storage at −80° C.

Selenomethionine Substituted β-Glucuronidase.

To express selenomethionine-substituted enzyme, B834 competent cells were transformed with pET-28a containing the β-glucuronidase gene. SelenoMet™ Medium and Nutrient Mix (AthenaES) was prepared for growth, with 50 mg of selenomethionine added for each liter of medium. The cells were grown at 37° C. until an $OD_{600}$ of 0.6 was reached and then were induced with 0.3 mM IPTG. The temperature was lowered to 15° C. and the cultures were grown overnight with shaking. Purification was performed as for the wild-type enzyme (see above).

Crystallization, Data Collection, and Phasing.

Crystals of E. coli β-glucuronidase were obtained at 2 mg/mL protein in 15% PEG3350, 0.2 M Magnesium Acetate, and 0.02% Sodium Azide at 16° C. Crystals first appeared after 5 days, and grew to a final size of approximately 100× 100×50 μm. (Pommier, 2006). Crystals were cryo-protected with perfluoropolyether vacuum pump oil (Sigma) and flash cooled in liquid nitrogen. Diffraction data were collected on the 22-BM beam line at SER-CAT (Advanced Photon Source, Argonne National Laboratory). Data was indexed and scaled using HKL2000. The crystals exhibited a space group C2, and the asymmetric unit contained two monomers. Selenomethionine data were collected to 2.9 Å and processed similarly. The PHENIX software suite (AutoSol) was utilized to locate heavy atom sites and to trace a portion of the model. An initial model was built by hand in Coot using the SAD data and later used with Phaser for molecular replacement with a native data set and the inhibitor bound structure. The structure was refined using simulated annealing and torsion angle refinement with the maximum likelihood function target in CNS, and monitored using both the crystallographic R and cross-validating R-free statistics. Data collection and refinement statistics are presented in Table 1. The software suite PHENIX was used for anisotropic B-factor and TLS refinement. The model was manually adjusted using Coot and $2F_o-F_c$ and $F_o-F_c$ electron density maps. The glucaro-δ-lactam model and definition files were generated using PRODRG, and after a ligand search using Coot, was easily placed into electron density in the active site of both monomers.

Inhibitor Compounds.

Purified protein was sent to NCCU-BRTTE to screen various compound libraries for potential inhibitors. Nine compounds were chosen for further analysis. The compounds (FIG. 3A) were purchased from ASINEX. Each compound was provided as a solid powder and dissolved in 100% dimethyl sulfoxide (DMSO) to various concentrations.

In Vitro β-Glucuronidase Assays.

In vitro assays were conducted at 50 μL total volume in 96-well, clear bottom assay plates (Costar). Reactions consisted of the following: ten microliters Assay Buffer (5 μL of 5% DMSO, and 5 μl, of 500 mM HEPES, pH 7.4), 30 μL substrate (various concentrations), 5 μL of an inhibitor solution (various concentrations), and 5 μL of 5 nM enzyme. Substrates used consisted of p-nitrophenyl glucuronide (PNPG) and phenolphthalein glucuronide (PheG) (FIG. 8) and were acquired from Sigma. The presence of the hydrolysis product of each, p-nitrophenol (PNP) and phenolphthalein (Phe), was measured by absorbance at 410 nm or 540 nm, respectively. Reactions were allowed to proceed for 6 hours at 37° C. and were quenched with 100 μL of 0.2 M sodium carbonate. Absorbance was measured using a PHERAstar Plus microplate reader (BMG Labtech). Data acquired was analyzed using Microsoft Excel and Sigmaplot 11.0.

Human Cell Survivability.

The nine compounds were tested for cytotoxicity in human cells. HCT116 human epithelial colonic cells were grown and cultured in DMEM medium till confluent and adherent. Cells were counted and the appropriate dilutions were made to achieve a 50,000 cell count per reaction. The HCT116 cells were aliquoted onto a 96-well assay plate and allowed to incubate at 37° C. in media for 16 hours prior to treatment with inhibitors. After incubation, 1 μL of each inhibitor, to achieve a final concentration of 100 were added to the cells and further incubated for 6 hours. Using the CellQuanti-Blue™ Cell Viability Assay Kit (BioAssay Systems), 10 μl, of the CellQuanti-Blue™ Reagent was added to each reaction and incubated at 37° C. for 2 hours. After incubation with the reagent, fluorescence was measured with excitation at 544 nm and emission at 590 nm.

Mammalian β-Glucuronidase In Vitro Assays.

Bovine liver β-glucuronidase was acquired in lyophilized form from Sigma. The protein was dissolved and the assay was conducted as previously published, using PNPG as the primary substrate for enzyme activity detection. The reaction mixture contained 1 μM bovine liver β-glucuronidase and 1 mM PNPG substrate. Each of the nine inhibitors were tested for an effect on mammalian β-glucuronidase activity by adding a concentration range of 0 to 100 μM to the reaction mixture. The reaction was allowed to proceed for 6 hours and then quenched with 0.2 M Sodium Carbonate. Absorbance was measured at the appropriate wavelength, and the data analyzed using Microsoft Excel and SigmaPlot 11.0.

Cell-Based Inhibition Assays.

HB101 E. coli cells, transformed with the pET-28a vector containing the β-Glucuronidase gene, were grown to an $OD_{600}$ of 0.6 in LB medium. The cells were then used in the in vivo assays to assess the glucuronidase activity and efficacy of the inhibitors. This assay was performed in a similar manner to the in vitro assay: ten microliters of substrate, 1 μL of inhibitor solution, and 40 μL of cells. Again, after 6 hours of incubation at 37° C., the reaction was quenched with 100 μL of 0.2 M Sodium Carbonate. A β-glucuronidase gene (GUS) knockout cell-line (GMS407) was purchased from CGSC at Yale University. Absorbance was measured at the appropriate wavelength, either 410 nm or 540 nm. Cell survivability in the presence of the nine inhibitors was assessed by plating a $10^{-5}$ dilution of 200 μl of saturated cells after incubation with 100 μM of each inhibitor for 6 hours. In addition, 1 mM of each hydrolysis product, 10 nM Tetracycline, and 2% DMSO (maximum concentration of DMSO when 100 μM inhibitor is added) were also tested for inhibitor effects on cell growth. Plated cells were allowed to incubate at 37° C. overnight, and colonies were counted to quantify the viability of the cells.

Anaerobic In Vivo Studies.

For the anaerobic cell lines used, two types of growth medium and agar plates were prepared: MRS medium/agar was used for Lactobacillus reuteri and Bifidobacterium infantis, and BHI medium/agar for Bacteroides vulgatus and Clostridium ramosum. Anaerobic cell lines were graciously provided by the Sartor Lab at the University of North Carolina at Chapel Hill. MRS agar plates were prepared by combining MRS and agar powder, as well as 0.1 g L-cysteine. BHI plates were produced in a similar manner with the addition of 0.2 mL each of 5 mg/mL heroin and 0.1% resazurin. Prior to streaking, plates were pre-equilibrated in an oxygen-free environment created in an anaerobic chamber and using the BD BBL™ GasPak™ Plus Anaerobic System Envelopes. One day before an assay was conducted, 5 mL overnight cultures, using the appropriate medium, were grown with no antibiotic present. Assay plates were prepared similar to the E. coli cell studies, and the reaction was allowed to progress in the anaerobic chamber for 6 hours. Absorbance data was collected after the reaction was quenched and analyzed.

All publications and patent applications mentioned in the specification am indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A method for attenuating side effects in a subject being administered a camptothecin-derived antineoplastic agent, the method comprising administering prior to, concurrently with or after administration of a camptothecin-derived antineoplastic agent a therapeutically effective amount of at least one selective enteric bacterial β-glucuronidase inhibitor, wherein said side effects are symptoms of gastrointestinal distress.

2. The method of claim 1, wherein said camptothecin-derived antineoplastic agent inhibits topoisomerase I.

3. The method of claim 1, wherein said camptothecin-derived antineoplastic agent is selected from the group consisting of camptothecin, diflomotecan, exatecan, gimatecan, irinotecan, karenitecin, lurtotecan, rubitecan, silatecan and topotecan.

4. The method of claim 3, wherein said camptothecin-derived antineoplastic agent is camptothecin or irinotecan.

5. The method of claim 1, wherein said selective enteric bacterial β-glucuronidase inhibitor is administered prior to said administration of a camptothecin-derived antineoplastic agent.

6. The method of claim 1, wherein said selective enteric bacterial β-glucuronidase inhibitor is administered concurrently with said administration of a camptothecin-derived antineoplastic agent.

7. The method of claim 1, wherein said selective enteric bacterial β-glucuronidase inhibitor is administered after said administration of a camptothecin-derived antineoplastic agent.

8. The method of claim 1, wherein said selective enteric bacterial β-glucuronidase inhibitor is administered within about two weeks of said administration of a camptothecin-derived antineoplastic agent.

9. The method of claim 8, wherein said selective enteric bacterial β-glucuronidase inhibitor is administered within about 1 day of said administration of a camptothecin-derived antineoplastic agent.

10. The method of claim 9, wherein said selective enteric bacterial β-glucuronidase inhibitor is administered within about 12 hours of said administration of a camptothecin-derived antineoplastic agent.

11. The method of claim 1, wherein at said effective amount said selective enteric bacterial β-glucuronidase inhibitor does not inhibit mammalian β-glucuronidases, wherein said attenuated side effect is gastrointestinal distress of said subject.

12. The method of claim 1, wherein said at least one selective enteric bacterial β-glucuronidase inhibitor is administered to the subject at a concentration from about 1 nM to about 1 mM.

13. The method of claim 1, wherein said enteric bacteria are selected from the group consisting of a *Bacteroides* sp., *Bifidobacterium* sp., *Catenabacterium* sp., *Clostridium* sp., *Corynebacterium* sp., *Enterococcus faecalis*, Enterobacteriaceae, *Lactobacillus* sp., *Peptostreptococcus* sp., *Propionibacterium* sp., *Proteus* sp., *Mycobacterium* sp., *Pseudomonas* sp., *Staphylococcus* sp. and *Streptococcus* sp.

14. The method of claim 1, wherein said selective enteric bacterial β-glucuronidase inhibitor exhibits selectivity for bacterial β-glucuronidases over mammalian β-glucuronidases and the $IC_{50}$ mammalian-$IC_{50}$ bacterial ratio is greater than 1.

15. The method of claim 14, wherein said $IC_{50}$ mammalian-$IC_{50}$ bacterial ratio is up to about $1 \times 10^5$.

16. The method of claim 14, wherein said $IC_{50}$ mammalian-$IC_{50}$ bacterial ratio is at least $1 \times 10^5$.

* * * * *